US009127130B2

(12) United States Patent
Krippner et al.

(10) Patent No.: US 9,127,130 B2
(45) Date of Patent: Sep. 8, 2015

(54) POLYLYSINE DENDRIMER CONTRAST AGENT

(75) Inventors: Guy Yeoman Krippner, Newtown (AU); Zemin Wu, Doncaster East (AU); Karlheinz Peter, Hawthorn East (AU); Christoph Hagemeyer, Cheltenham (AU); David Owen, Vermont South (AU)

(73) Assignees: STARPHARMA PTY LTD., Abbotsford, Vic (AU); BAKER IDI HEART AND DIABETES INSTITUTE HOLDINGS LTD, Melbourne, Vic (AU)

( * ) Notice: Subject to any disclaimer, the term of this patent is extended or adjusted under 35 U.S.C. 154(b) by 1422 days.

(21) Appl. No.: 12/377,252

(22) PCT Filed: Aug. 10, 2007

(86) PCT No.: PCT/AU2007/001122
§ 371 (c)(1),
(2), (4) Date: Jul. 8, 2010

(87) PCT Pub. No.: WO2008/017122
PCT Pub. Date: Feb. 14, 2008

(65) Prior Publication Data
US 2010/0278750 A1    Nov. 4, 2010

(30) Foreign Application Priority Data

Aug. 11, 2006 (AU) .............................. 2006904385
Apr. 2, 2007 (AU) .............................. 2007901752

(51) Int. Cl.
*A61K 9/14*     (2006.01)
*C08G 83/00*    (2006.01)
(Continued)

(52) U.S. Cl.
CPC ............. *C08G 83/003* (2013.01); *A61K 47/487* (2013.01); *A61K 47/48253* (2013.01); *A61K 47/48561* (2013.01); *A61K 49/124* (2013.01);
(Continued)

(58) Field of Classification Search
CPC ....................................................... A61K 49/16
See application file for complete search history.

(56) References Cited

U.S. PATENT DOCUMENTS

| 5,229,490 | A | 7/1993 | Tam | |
| 7,985,424 | B2 * | 7/2011 | Tomalia et al. | 424/486 |
| 2007/0248547 | A1 * | 10/2007 | Brasch et al. | 424/9.322 |

FOREIGN PATENT DOCUMENTS

| AU | 2002245932 B2 | 4/2007 |
| EP | 0 884 327 B1 | 3/2001 |

(Continued)

OTHER PUBLICATIONS

Choi, J.S. et al. 2000 "Synthesis of a Barbell-like triblock copolymer, poly(L-lysine) dendrimer-blockpolyethylene glycol)-block-poly(L-lysine) dendrimer, and its self-assembly with plasmid DNA" *J. Am. Chem. Soc.* 122: 474-480.

(Continued)

*Primary Examiner* — Paul Dickinson
(74) *Attorney, Agent, or Firm* — Knobbe, Martens, Olson & Bear, LLP

(57) ABSTRACT

The present invention relates generally to branched macromolecules and their use as imaging or contrast agents. In particular, the invention relates to dendrimers, derived from lysine or lysine analogs, bearing a plurality of functional moieties and their application to imaging techniques in which a disease state may be imaged with a targeted contrast agent.

30 Claims, 3 Drawing Sheets

C terminal Cysteine sequence pMT/BiP/V5-His M—LIBS-C

TATGAAGTTATGCATATTACTGGCCGTCGTGGCCTTTGTTGGCCTCTCGCTCGG
GAGATCggCCATGGCGCAGGTGCAGCTGCAGCAGTCTGGGGGAGGCTTAGTGA
AGCCTGGAGGGTCCCTGAAACTCTCCTGCGCAGCCTCTGGATTCACTTTCAGTA
GCTATATCATGTCTTGGGTTCGCCAGACTCCGAGAAGAGGCTGGAGTGGGTC
GCAACCATTAGAAGTGGTGGTGATAACACCTACTATCCAGACAGTGTGAAGGG
TCGATTCACCATCTCCAGAGACAATGCCAAGAACAAGTTGTACCTGCAAATGA
GCAGTCTGAGGTCTGAGGACACGGCCTTGTATTACTGTGCAATCTACTATGGT
AACTACGGGGGCTTGCTTACTGGGGCCAAGGGACTCTGGTCACTGTCTCTGC
AGCCAAAACGACACCCAAGCTTGAAGAAGGTGAATTTTCAGAAGCACGCGTA
GATATCTTGATGACCCAATCTCCAGCCTCCCTATCTGCATCTGTGGGAGAAACT
GTCACCATCACATGTCGAGCAAGTGGGAATATTCACAATTATTTAGCATGGTA
TCAGCAGAAACAGGGAAAATCTCCTCAGCTCCTGGTCTATAATGCAAAAACCT
TAGCAGATGGTGTGCCATCAAGGTTCAGTGGCAGTGGATCAGGAACACAATAT
TCTCTCAAGATCAACAGCCTGCAGCCTGAAGATTTTGGGAGTTATTACTGTCAA
CATTTTTGGAGTACTCCGTACACGTTCGGAGGGGGGACCAAGCTGGAAATAAA
ACGGGCTGATGCTGCGGCCGCttCTAGAGGGCCCTTCGAAGGTAAGCCTATCCC
TAACCCTCTCCTCGGTCTCGATTCTACGCGTACCGGTCATCATCACCATCACCA
CggagggtgcaTGCTGA

(51) Int. Cl.
| | |
|---|---|
| A61K 47/48 | (2006.01) |
| A61K 49/12 | (2006.01) |
| A61K 49/16 | (2006.01) |
| C08G 69/10 | (2006.01) |
| C08G 73/02 | (2006.01) |
| C08L 77/04 | (2006.01) |

(52) U.S. Cl.
CPC ............. *A61K 49/16* (2013.01); *C08G 69/10* (2013.01); *C08G 73/028* (2013.01); *C08L 77/04* (2013.01)

(56) References Cited

FOREIGN PATENT DOCUMENTS

| | | |
|---|---|---|
| WO | WO 99/01160 A1 | 1/1998 |
| WO | 9843677 A1 | 10/1998 |
| WO | 02079299 A1 | 10/2002 |
| WO | 03089010 A1 | 10/2003 |
| WO | WO 2007048186 A1 * 5/2007 ............. C07K 16/28 |

OTHER PUBLICATIONS

Kurita, T. et al. 1999 "Syntheses and biological activities of dendrimeric mastoparans" *Chemistry Letters* 3:193-194.

Qualmann, B. et al. 1996 "Synthesis of Boron-Rich Lysine Dendrimers as Protein Labels in Electron Microscopy" *Angewandte Chemie International Edition in English* 8:909-911.

Ramaswamy, C. et al. 2003 Dendriplexes and their characterisation *Int. J. of Pharmaceutics* 254:1721.

Roy, R. and Baek, M.-G. 2002 "Glycodendrimers: novel glycotope isosteres unmasking sugar coding. Case study with T-antigen markers from breast cancer MUC1 glycoprotein" *Reviews in Molecular Biotechnology* 90: 291-309.

Vlasov, G. et al. 2004 "Lysine dendrimers and their starburst polymer derivatives: possible application for DNA compaction and in vitro delivery of genetic constructs" *Russian J. of Bioorg. Chem.* 30 (1): 12-20.

European Supplementary Search Report dated Aug. 1, 2012 and issued for European Patent Application 07 784 762.2.

Gaëlle Nicolle, et al., "The Impact of Rigidity and Water Exchange on the Relaxivity of a Dendritic MRI Contrast Agent", Chemistry—A European Journal, 2002, vol. 8, No. 5, pp. 1040-1048.

Tae-il Kim et al., "PAMAM-PEG PAMAM: Novel Triblock Copolymer as a Biocompatible and Efficient Gene Delivery Carrier", Biomacromolecules, 2004, vol. 5, pp. 2487-2492.

B. Qualmann et al., "Electron spectroscopic imaging of antigens by reaction with boronated antibodies", Journal of Microscopy, vol. 83, Part 1, Jul. 1996, pp. 69-77.

Kurita Takashi, et al., "Syntheses and Biological Activities of Dendrimeric Mastoparans", Chemistry Letters, vol. 3, 1999, pp. 193-194.

* cited by examiner

Figure 1

C terminal Cysteine sequence pMT/BiP/V5-His M—LIBS-C

TATGAAGTTATGCATATTACTGGCCGTCGTGGCCTTTGTTGGCCTCTCGCTCGG
GAGATCggCCATGGCGCAGGTGCAGCTGCAGCAGTCTGGGGGAGGCTTAGTGA
AGCCTGGAGGGTCCCTGAAACTCTCCTGCGCAGCCTCTGGATTCACTTTCAGTA
GCTATATCATGTCTTGGGTTCGCCAGACTCCGGAGAAGAGGCTGGAGTGGGTC
GCAACCATTAGAAGTGGTGGTGATAACACCTACTATCCAGACAGTGTGAAGGG
TCGATTCACCATCTCCAGAGACAATGCCAAGAACAAGTTGTACCTGCAAATGA
GCAGTCTGAGGTCTGAGGACACGGCCTTGTATTACTGTGCAATCTACTATGGT
AACTACGGGGGCTTGCTTACTGGGGCCAAGGGACTCTGGTCACTGTCTCTGC
AGCCAAAACGACACCCAAGCTTGAAGAAGGTGAATTTTCAGAAGCACGCGTA
GATATCTTGATGACCCAATCTCCAGCCTCCCTATCTGCATCTGTGGGAGAAACT
GTCACCATCACATGTCGAGCAAGTGGGAATATTCACAATTATTTAGCATGGTA
TCAGCAGAAACAGGGAAAATCTCCTCAGCTCCTGGTCTATAATGCAAAAACCT
TAGCAGATGGTGTGCCATCAAGGTTCAGTGGCAGTGGATCAGGAACACAATAT
TCTCTCAAGATCAACAGCCTGCAGCCTGAAGATTTTGGGAGTTATTACTGTCAA
CATTTTTGGAGTACTCCGTACACGTTCGGAGGGGGGACCAAGCTGGAAATAAA
ACGGGCTGATGCTGCGGCCGCttCTAGAGGGCCCTTCGAAGGTAAGCCTATCCC
TAACCCTCTCCTCGGTCTCGATTCTACGCGTACCGGTCATCATCACCATCACCA
CggaggtgcaTGCTGA

Figure 2

C-terminal Q-tag

ATGAAGTTATGCATATTACTGGCCGTCGTGGCCTTTGTTGGCCTCTCGCTCGGG
AGATCggCCATGGCGCAGGTGCAGCTGCAGCAGTCTGGGGGAGGCTTAGTGAA
GCCTGGAGGGTCCCTGAAACTCTCCTGCGCAGCCTCTGGATTCACTTTCAGTAG
CTATATCATGTCTTGGGTTCGCCAGACTCCGGAGAAGAGGCTGGAGTGGGTCG
CAACCATTAGAAGTGGTGGTGATAACACCTACTATCCAGACAGTGTGAAGGGT
CGATTCACCATCTCCAGAGACAATGCCAAGAACAAGTTGTACCTGCAAATGAG
CAGTCTGAGGTCTGAGGACACGGCCTTGTATTACTGTGCAATCTACTATGGTA
ACTACGGGGGGCTTGCTTACTGGGGCCAAGGGACTCTGGTCACTGTCTCTGCA
GCCAAAACGACACCCAAGCTTGAAGAAGGTGAATTTTCAGAAGCACGCGTAG
ATATCTTGATGACCCAATCTCCAGCCTCCCTATCTGCATCTGTGGGAGAAACTG
TCACCATCACATGTCGAGCAAGTGGGAATATTCACAATTATTTAGCATGGTAT
CAGCAGAAACAGGGAAAATCTCCTCAGCTCCTGGTCTATAATGCAAAAACCTT
AGCAGATGGTGTGCCATCAAGGTTCAGTGGCAGTGGATCAGGAACACAATATT
CTCTCAAGATCAACAGCCTGCAGCCTGAAGATTTTGGGAGTTATTACTGTCAA
CATTTTTGGAGTACTCCGTACACGTTCGGAGGGGGGACCAAGCTGGAAATAAA
ACGGGCTGATGCTGCGGCCGCttCTAGAGGGCCCTTCGAAGGTAAGCCTATCCC
TAACCCTCTCCTCGGTCTCGATTCTACGCGTACCGGTCATCATCACCATCACCA
CggaggtgcaCCGAAACCTCAACAGTTCATGTGA

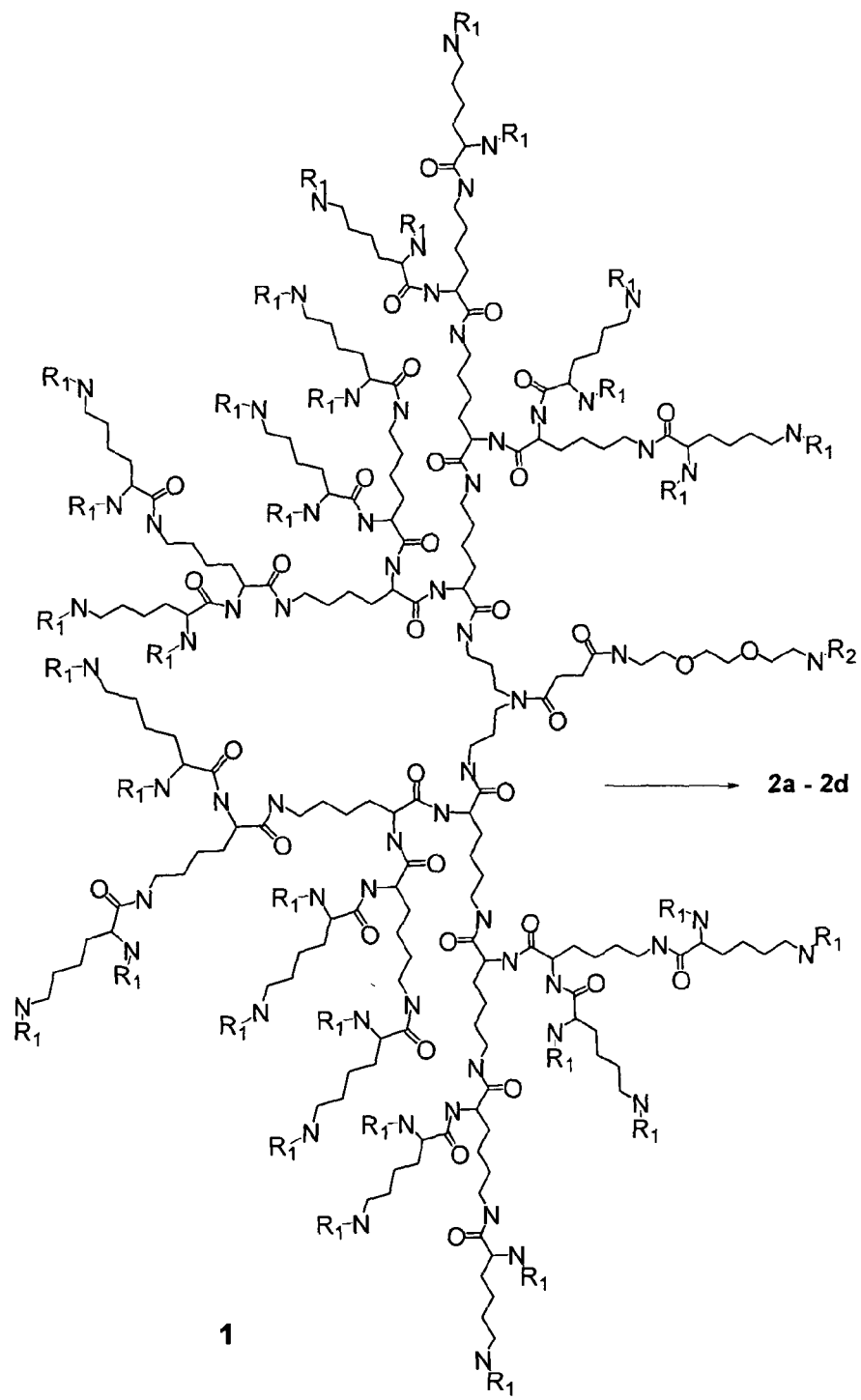
Figure 3: 1: $R_1$ = Boc, $R_2$ = Cbz, Products and Conditions: 2a ($R_1$ = H, $R_2$ = Cbz), TFA/acetic acid; 2b( $R_1$ = Gd-GlyMeDOTA, $R_2$ = Cbz), Gd-GlyMeDOTA NHS ester, DMSO; 2c( $R_1$ = Gd-GlyMeDOTA, $R_2$ = H), Pd/C, ammonium formate, DMF/H$_2$O; 2d( $R_1$ = Gd-GlyMeDOTA, $R_2$ = COC2-MA), 3-maleimidopropanoic acid NHS ester, DIPEA, DMSO.

POLYLYSINE DENDRIMER CONTRAST AGENT

This application is U.S. National Phase of International Application PCT/AU2007/001122, filed Aug. 10, 2007 designating the U.S., and published in English as WO 2008/017122 on Feb. 14, 2008, which claims priority to Australian Patent Application No. 2006904358, filed Aug. 11, 2006 and Australian Patent Application No. 2007901752, filed Apr. 2, 2007.

FIELD OF THE INVENTION

The present invention relates generally to branched macromolecules and their use as imaging or contrast agents in diagnostic applications. In particular, the invention relates to dendrimers, derived from lysine or lysine analogues, bearing a plurality of functional moieties and their application to imaging techniques in which a disease state may be imaged with a targeted contrast agent.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Diagnostic imaging techniques, such as magnetic resonance imaging (MRI), X-ray, nuclear radiopharmaceutical imaging, ultraviolet-visible-infrared light imaging, and ultrasound, have been used in medical diagnoses for many years. MRI and optical imaging methods are unique among imaging modalities in that they yield complex signals that are sensitive to chemical environment.

Magnetic Resonance Imaging (MRI) obtains images of the body in thin slices by measuring the characteristics of hydrogen nuclei of water (and nuclei with similar chemical shifts), modified by chemical environment across the slice. The signal intensity depends on the amount of water in a given place and on the magnetic relaxation times. It is this latter characteristic that can be manipulated with the use of contrast agents to change the signal intensity and the appearance of different tissues on the MR image.

Contrast agents are chemical substances introduced to the anatomical or functional region being imaged, to increase the differences between different tissues or between normal and abnormal tissue, by altering the relaxation times.

Achieving sufficient sensitivity is a significant problem for MRI in particular, where concentrations in the range of 10-1000 μM of the image enhancing moiety are required to produce an adequate signal. Accordingly, targeted agents may be utilised which deliver concentrations of the imaging agent to the target so that sufficient improvement in the signal is observed during the course of imaging. Even then however, the problem can be further complicated for targeted agents if the desired target is present at low concentrations. For example, in order to image biological receptor targets that are present at less than μM concentrations, great signal enhancement is required at the target site to prove sufficient image contrast.

The most commonly used contrast-enhancing agents are paramagnetic species such as metal ions. Gadolinium (Gd) is preferred because it has seven unpaired electrons that produced an especially short paramagnetic effect on adjacent water protons. Since paramagnetic metal ions useful for relaxivity enhancement are usually toxic, placing such ions in physiological compatible complexes reduces their toxicity without substantially reducing their effectiveness.

Presentation of a plurality of paramagnetic particles enhances the use of a contrast-enhancing agent. It also reduces the amount of contrast agent actually required compared to agents having macromolecules bearing fewer particles. For example, it is believed that a 50% reduction in T1 relaxation time of water protons in a target tissue is a requirement for an effective MRI contrast agent. Analysis of tumor enhancement for MRI using an antibody conjugated with 4 Gd atoms per antibody molecule found no tumor enhancement and predicted that a far greater ratio of imaging metal atoins per macromolecule would be required.

Conventional MRI contrast-enhancing agents have only one chelant per molecule. These agents are typically short-lived in the subject's body or other physiological environments. Thus, in many instances, large doses must be administered in order to achieve a desired degree of contrast enhancement. In other instances, maximal contrast enhancement cannot be achieved without administering a potentially fatal or otherwise physiologically intolerable dose to the subject.

There exists a need therefore, for new imaging agents which may advantageously provide multiple signalling or imaging entities and/or specifically target cell or tissue types.

SUMMARY OF THE INVENTION

It has now been found that macromolecules bearing a plurality of imaging or signalling entities and at least one functionality which targets the macromolecule to a site intended for imaging may provide useful imaging agents.

Accordingly first aspect of the invention provides a macromolecule comprising:
(i) a core moiety having a first amino nitrogen atom for attachment to a first functional moiety and at least two further amino nitrogen atoms for attachment to lysine or lysine analogue building units;
(ii) a first functional moiety attached to the core moiety through the first amino nitrogen atom;
(iii) at least one layer of lysine or lysine analogue building units, the outermost layer having surface amino nitrogen atoms for attachment to one or more second functional moieties, said layers attached to the core moiety through the at least two further amino nitrogen atoms of the core moiety; and
(iv) one or more second functional moieties attached to the surface amino nitrogen atoms of the outermost layer of lysine or lysine analogue building units;

wherein
the first and second functional moieties each comprise an agent selected from the group consisting of a targeting molecule and a signalling entity such that the macromolecule has at least one targeting molecule and at least one signalling entity.

The invention further relates to the use of a macromolecule according to the invention in diagnostic imaging, particularly MRI contrast imaging.

Preferably the targeting molecule is a peptide or antibody, more preferably a peptide or antibody capable of targeting receptors and markers expressed on cells. Targeting may improve the concentration of the lysine or lysine analogue dendrimer polymer of the invention at a designated target site, advantageously resulting in the administration of lower amounts of imaging agent.

The lysine dendrimer may advantageously be suitable for, amongst other things, use as a contrast agent with adequate image enhancement, prolonged intravascular retention and improved tissue targeting.

In certain embodiments of the invention, the first functional moiety is a targeting molecule and the second functional moiety is a signalling entity.

In some embodiments of the invention, the targeting molecule is capable of selectively binding or interacting to one or more of:
 (a) activated leukocytes;
 (b) activated platelets;
 (c) fibrin; or
 (d) activated endothelial cells.

Surprisingly, the applicants have discovered that in some embodiments, a contrast agent may exhibit both improved image definition and target specificity when utilised in diagnostic applications, including magnetic resonance imaging (MRI) and the like.

A plurality of signalling entities of a macromolecule may constitute the same or different entities. In certain embodiments of the invention the signalling entities are paramagnetic particles, such as paramagnetic metal ions, which may advantageously be chelated to the lysine or lysine analogue dendrimer polymer through a chelant.

The macromolecule may contain only first and second functional moieties or may include one or more third (and optionally fourth or fifth) functional moieties as defined herein. Thus, the macromolecule may contain a targeting molecule as a first functional moiety, a plurality of (second functional moiety) signalling entities and at least one third functional moiety, which may be a different signalling entity to the second functional moiety or the same or different targeting molecule to the first targeting molecule.

The targeting molecule and the signalling moiety may be attached directly to the appropriate nitrogen atom (surface or core) or indirectly, by virtue of a linker and/or modifying group which facilitates the attachment.

The macromolecules may advantageously be prepared by attaching the targeting molecule to the first amino nitrogen atom of the core moiety of a dendrimer and attaching one or more signalling moieties to the surface of the dendrimer.

Accordingly, in another aspect, the invention provides a process for preparing a dendrimer polymer bearing a targeting molecule as described above, the process including the steps of:
 providing
 (a) a dendrimer polymer including;
  (i) a core moiety having a first amino nitrogen atom for attachment to a first functional moiety and at least two further amino nitrogen atoms for attachment to lysine or lysine analogue building units;
  (ii) at least one layer of lysine or lysine analogue building units, the outermost layer having surface amino nitrogen atoms for attachment to one or more second functional moieties, said layers attached to the core moiety through the at least two further amino nitrogen atoms of the core moiety; and
 (b) a targeting molecule;
 and attaching the targeting molecule to the first amino nitrogen atom of the core or surface amino nitrogen atom.

In certain embodiments of the invention, the targeting molecule is attached to the first amino nitrogen atom of the core, Optionally, the first nitrogen atom and/or the targeting molecule may be modified by a modifier moiety to facilitate the attachment.

Signalling entities may then be attached to the surface of the dendrimer.

Thus, the invention also provides a macromolecule comprising:
 (i) a core moiety having a first amino nitrogen atom for attachment to a first functional moiety and at least two further amino nitrogen atoms for attachment to lysine or lysine analogue building units;
 (ii) a targeting molecule attached to the core moiety through the first nitrogen atom; and
 (iii) at least one layer of lysine or lysine analogue building units, the outermost layer having surface amino nitrogen atoms for attachment to one or more second functional moieties, said layers attached to the core moiety through the at least two further amino nitrogen atoms of the core moiety;
wherein the surface amino nitrogen atoms of the outermost layer of building units are capable of bearing a plurality of signalling entities.

In a further aspect of the invention, there is provided a method for imaging, such as magnetic resonance imaging, of a cellular target in a mammal, the method including the steps of
 (a) administering to a mammal an imaging agent according to the invention;
 (b) allowing the imaging agent to bind to the cellular target; and
 (c) imaging the mammal to generate an image.

In certain embodiments, the imaging agent is a contrast agent and the image is obtained by MRI. The method for MR imaging of a cellular target in a mammal may be utilised to detect cellular targets that are indicators of disease or conditions.

In certain embodiments of the invention, the disease or condition is a blood coagulation disorder, or an inflammatory condition such as early stage atherosclerosis.

BRIEF DESCRIPTION OF THE DRAWINGS

FIG. 1 shows the sequence (pMT/BiP/V5-His M-LIBS-C) based on the LIDS antibody (described in PCT/AU2006/000943) with an extra C-terminal Cysteine introduced by standards molecular biology techniques for coupling purpose.

FIG. 2 shows the sequence (pHOG-LIBS-His-gga-QQ) based on the LIBS antibody (described in PCT/AU2006/000943) with a Q tag introduced by standards molecular biology techniques for coupling purpose.

FIG. 3 shows a reaction scheme for the preparation of [COC2-MA] NEOEOEN[Su(NPN)$_2$][Lys]$_{16}$[Gd-GlyMeDOTA]$_{32}$, exemplified in Example 6.

DETAILED DESCRIPTION OR THE EMBODIMENTS

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

By the term "chelant" as used herein in the specification and claims we mean a moiety capable of binding a therapeutically or diagnostically useful metal ion.

The term "antibody" as used herein in the specification and claims includes the full antibody, or a derivative or a fragment, such as derived from enzymatic or chemical cleavage or obtained recombinantly, or a mimic of the binding region of an antibody produced either by way of protein expression techniques or through chemical synthesis, which retains the specific binding activity in particular, the term includes monoclonal antibodies and all the various forms derived from monoclonal antibodies, including but not limited to full-length antibodies (e.g. having an intact Fc region), antigen-binding fragments, including for example, Fv, Fab, Fab' and F(ab'), fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies and humanized antibodies.

The term "attached" as used herein in the specification and claims refers to a connection between chemical components of the macromolecule by way of covalent bonding, hydrogen bonding, adsorption, metallic bonding, Van der Walls forces, ionic bonding, chelate-metal-chelate linkages, a ligand-receptor linkages, duplexes or triplexes formed from complimentary strands of DNA, RNA of peptide analogues thereof, or any combination thereof. A particular form contemplated herein is covalent bonding. The attachment may be direct, or indirect through an intervening moiety or moieties, such as a bridge, spacer, or linker moiety or moieties, which terms may be used interchangeably herein. Furthermore, a linker group or functional moiety or amine may be further modified by a modifier to facilitate the attachment.

By the term "activated" as used herein in the specification and claims, and when used in relation to particular targeting molecules, we mean any form of the particular targeting molecule that is capable of reacting with a ligand involved in a process.

By the term "binding" as used herein in the specification and claims we mean the ability of a given polypeptide to interact with a receptor such that the interaction between the polypeptide antibody or derivatives thereof and the receptor is relatively specific.

The term "derivatives" as used herein in the specification and claims, and when used in relation to polypeptides, particularly antibodies refers to functional equivalents having similar amino acid sequence, say at least 80, 85, 90, or 95% homology, and retaining, at least to some extent, the activities of the polypeptide.

The term "surface" as used herein, is used in reference to the outermost layer of building units of the dendrimer.

The term "surface building unit" as used herein in the specification and claims refers to the outermost layer of building units of the macromolecule, i.e. there are no further building Units attached to the surface amities of a surface building unit.

The term "surface amine" or "surface amino" or "surface amino nitrogen atom" as used herein in the specification and claims refers to any of the outer-most nitrogens of the dendritic motif which derive from surface building units. These surface amines represent the points of attachment for additional building units, linkers or functional moieties optionally via a modifier group.

The term "lysine analogue" as used herein in the specification and claims refers to a molecule which has a single apex carboxyl group and two or three primary amine groups. In one instance they may be asymmetric, as for the parent Lysine 1 and this is defined as meaning that the bonds and atoms that join the primary amines to the carboxylate apex are different. In a second instance lysine analogues may be symmetrical which is defined to mean that the bonds and atoms that join each primary amine to the carboxylate are identical, and which disregards the asymmetry that is potentially introduced when each primary amine is further reacted.

The term "dendritic motif" as used herein in the specification and claims refers to a discrete unit of the macromolecule. When one of the macromolecule branches is cut at the bond which connects one of the reactable amines of the building unit or core to the apex carboxylate group of the attached building unit, the dendritic motif will "fall out". The apex carboxylate group of the dendritic motif represents the point at which the dendritic motif would be attached to a growing macromolecule core during the process of synthesising a macromolecule of the invention.

The term "building unit" as used herein in the specification and claims refers to lysine or lysine analogues used in the assembly of dendritic motifs. The building unit may be a subsurface building unit, being part of the layer, or generation, of building units bearing amines that may be further reacted with the apex carboxylate group of a further building unit. The layers may in turn be described as the surface-but-one layer, meaning the first subsurface immediately adjacent the surface layer; the surface-but-two layer is the second layer below the surface layer; the surface-but-three layer is the third layer below the surface layer; and so on.

As used herein, the term "layer" or "generation" refers to a plurality of building units having the same degree of connectivity to the core moiety, i.e. having the same number of building units linking the building unit in question to the amino nitrogen atoms of the core. For example, building units which are attached, either directly or via a linker group, to the nitrogen atoms of the core moiety are referred to the first layer or generation. Building units which have one building unit between them and the nitrogen atoms of the core moiety are referred to as the second layer or generation. A layer or generation of building units must contain at least two building units. Each layer of building units is homogenous with regard to the building unit used, however, different building units may be used to prepare different layers. Thus in certain embodiments of the invention, the macromolecule is composed of one or more layers of a single type of building unit, e.g. lysine. In other embodiments, the macromolecule comprises at least two layers of building units wherein at least two layers are composed of different building units.

By the term "terminal surface amine" as used herein in the specification and claims we mean any surface reactable amine group of the dendron. Such groups are designated as terminal since they may act as the terminus or site of further dendrimeric or end stopping reactions.

By the term "terminal surface group" as used herein in the specification and claims we mean any protecting group, or organic radical which is attached to a surface amine. The nature and number of terminus-bearing surface amine groups may be determined by standard analytical techniques including proton/carbon NMR, ESI or MALDI mass spectrometry.

The term "amine-protecting groups", as used herein in the specification and claims refers to groups for which an order of removal exists such that those groups that are not meant for cleavage are inert to the cleavage conditions. When protecting groups are defined as "resolvable", this means that the conditions for removal of one group may affect the integrity of the second group and this requires that the second group be removed first if the integrity of the first group is to be maintained. When protecting groups are further defined as "orthogonal", this means that each group is inert to the cleavage conditions required to remove each of the other groups of the orthogonal set. It is important to note that protecting groups are resolvable or orthogonal only when the appropriate reaction conditions are used. Suitable protecting groups may be chosen from protecting groups including Boc, CBz, Fmoc, Dde, CF₃CO₂, 2-halo-Cbz, Aloe, MemSiEtSO₂, Troc, o-NO-₂PhSO₂, 2,4-dinitrobenzene-sulfonyl, and preferably from Boc, CBz, Fmoc 2-halo-Cbz, Aloc, Me₃SiEtSO₂, Troc, o-NO-₂PhSO₂, 2,4-dinitrobenzene-sulfonyl. There are general methods described in the art for the selective monoprotection of polyamine molecules. Such methods are described in Krapcho and Knell *Synthetic Commun.* (1990) 20:2559.

The macromolecules of the present invention are constructed from at least one layer of lysine or lysine analogue building units. Examples of building units contemplated by the invention include the following (where # depicts the carbonyl residue of the apex carboxyl group):

Lysine* 1 having the structure:

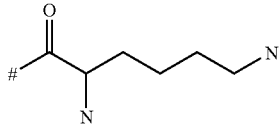

1

Glycyl-Lysine* 2 having the structure:

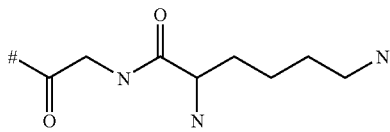

2

Analogue 3, having the structure below, where a is an integer 1 or 2; and b and c are independently integers 1, 2, 3 or 4.

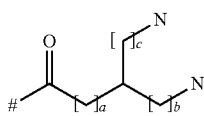

3

Analogue 4, having the structure below, where a is an integer 0, 1 or 2; and b and c are independently integers 2, 3, 4, 5 or 6

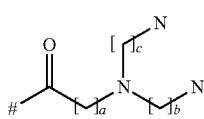

4

Analogue* 5, having the structure below, where a is an integer 0, 1, 2, 3, 4 or 5; and b and c are independently integers 1, 2, 3, 4 or 5

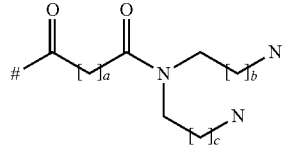

5

Analogue 6, having the structure below, where a is an integer 0, 1, 2, 3, 4 or 5; and b and c are independently integers 0, 1, 2, 3, 4 or 5

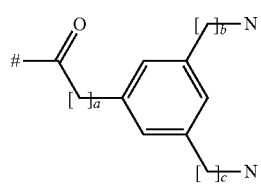

6

Analogue 7, having the structure below, where a is an integer 0, 1, 2, 3, 4 or 5; and b and c are independently integers 1, 2, 3, 4 or 5

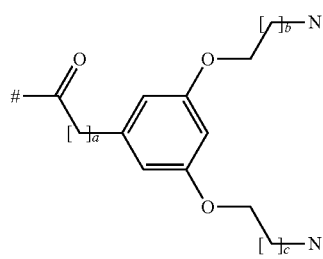

7

Analogue 8, having the structure below, where a is an integer 0, 1, 2, 3, 4 or 5; and b, c and d are independently integers 1, 2, 3, 4 or 5

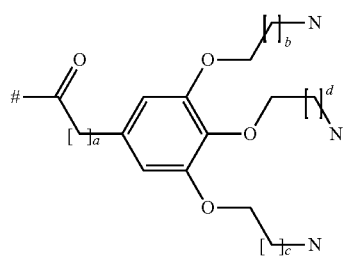

8

Analogue 9, having the structure below, where a is an integer 0, 1, 2, 3, 4 or 5; and b and c are independently integers 1, 2, 3, 4 or 5

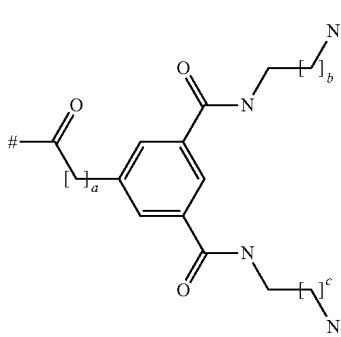

Furthermore, any methylene group of the building units may be replaced by a methyleneoxy (CH$_2$—O) or ethyleneoxy (CH$_2$—CH$_2$—O) group, provided that this does not result in the formation of a carbonate (—O—C(O)—O—) or carbamate (—O—C(O)—N—) moiety within the building unit.

In certain embodiments of the invention, the building units are selected from Lysine 1, Glycyl-Lysine 2 or Lysine analogue 5:

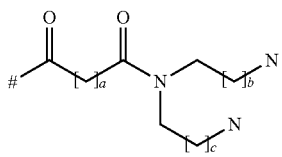

where a is an integer 0, 1 or 2 and further, any methylene group of 1, 2 or 5 may be replaced by a methyleneoxy or ethyleneoxy group provided that this does not result in the formation of a carbonate or carbamate moiety within the building unit.

Both the carboxylate group and the amine groups of the building units may be derivatised to enhance or diminish the reactivity of these groups. Reactable amine groups may be protected (deactivated) using amine-protecting groups such as Boc, CBz, 4-nitrobenzyloxycarbamate (4-NO$_2$—CBz) Fmoc, Dde, CF$_3$CO$_2$, 2-halo-CBz, Alloc, Me$_3$SiEtSO$_2$, Troc, o-NO-$_2$PhSO$_2$ and 2,4-dinitrobenzene-sulfonyl groups.

In general, a free carboxyl group is not sufficiently reactive to react with an amine to form the amide bond, so some means is preferably provided that facilitates the dehydration and so drives the reaction to completion. This may be achieved, for example, by "activating" the carboxyl group as an acyl halide derivative or an activated ester derivative (The Peptides, Analysis, Synthesis and Biology Vol 1 Major Methods of Peptide Bond Formation; Academic Press New York 1979 eds Gross, E. and Meienhofer, J., Peptides: Chemistry and Biology, Wiley-Val Weinheim 2002, Sewald, N. and Iakubke, H-D. The Chemical Synthesis of Peptides Clarendon Press, Oxford 1994, Jones, J.).

In the first activation method, the reagent which contains the carboxylic acid is reacted with a second reagent containing a hydroxyl moiety in the presence of a dehydrating reagent and, where required, other activating agents, to provide a product in which the acid containing moiety and the hydroxyl containing moiety are joined by an ester bond. This product is known as an "active ester". The reagent containing the hydroxyl moiety is chosen such that the product ester will readily react with primary amines to form amides with liberation of the aforementioned reagent containing the hydroxyl moiety. In some cases, the active ester is sufficiently stable to enable it to be isolated, purified and stored prior to use.

In a second activation method, the reagent which contains the carboxyl group may be reacted "in situ" with an activating agent to form an acyl species which further reacts with primary amines also present "in situ" or added after an appropriate prior activation time to lead to the formation of the required amide bond.

Both activation methods are described in more detail in PCT/AU2006/001591.

The lysine or lysine analogue building units of the dendritic motifs are reacted with a core compound. A core may be any compound containing three or more reactive (amino) nitrogens, one of which ultimately becomes the point of attachment for the first functional moiety (first amino nitrogen atom). It will be understood that this nitrogen atom can be protected by an appropriate protection group during construction of the dendrimer.

In certain embodiments of the invention, the core can be prepared by reacting one nitrogen atom of a diamino compound with lysine or a lysine analogue to form a triamino core compound. The unreacted amino group of the diamino compound can then become the amino group for attachment of the first functional moiety while the at least two amino groups of the lysine or lysine analogue become the points of attachment for the building units.

Diamino compounds suitable for reaction with lysine or lysine analogues, such as those exemplified herein, to prepare the core moieties include:

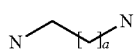

where a is an integer of 1 to 9, for example 1, 2, 3, 4 or 5;

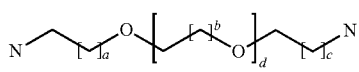

where a, b and c, are independently integers 1, 2, 3, 4 or 5, such as 2 or 3; and d is an integer from 0-100, such as 1-30; particularly 1-5, 6-10, 11-15, 16-20, 21-25 or 26-30;

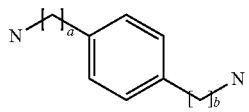

where a and b, are independently integers 0, 1, 2, 3, or 5;

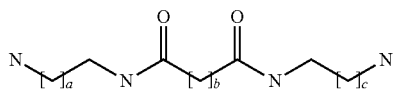

where a and c, are independently integers 1, 2, 3, 4, 5 or 6 and where b is an integer from 0, 1, 2, 3, 4, 5 or 6;

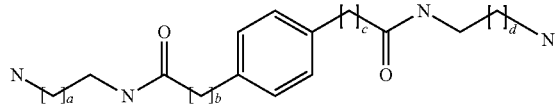

where a and d, are independently integers 1, 2, 3, 4, 5 or 6 and where b and c, are independently integers 0, 1, 2, 3, 4, 5 or 6.

Triamino compounds may be employed without further modification (i.e. reaction with lysine or a lysine analogue), or may be reacted with a lysine or lysine analogue to form a tetraamino core.

Examples of triamino compounds include:

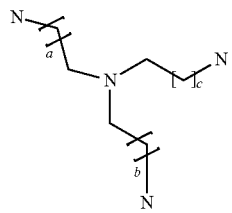

where a, b and c, are independently integers 1, 2, 3, 4, 5 or 6;

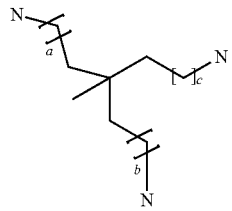

where a, b and c, are independently integers 0, 1, 2, 3, 4, 5 or 6;

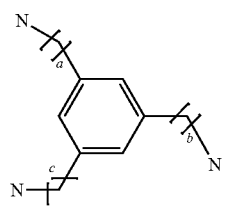

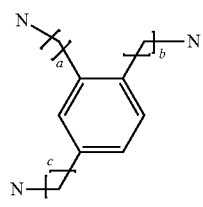

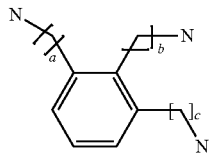

where a, b and c, are independently integers 0, 1, 2, 3, 4, 5 or 6;

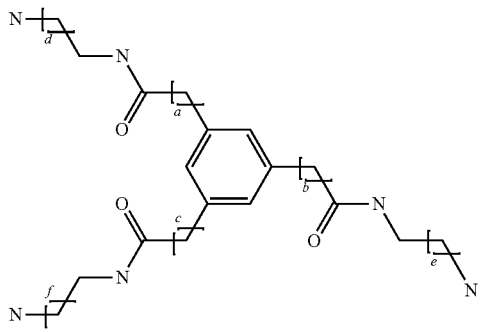

where a, b and c, are independently integers 0, 1, 2, 3, 4, 5 or 6; and d, e and f, are independently integers 1, 2, 3, 4, 5 or 6.

Tetramino compounds may be employed without further modification (i.e. reaction with lysine or a lysine analogue) or may be reacted with lysine or a lysine analogue to form a pentamino core. Examples of tetramino compounds include:

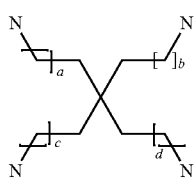

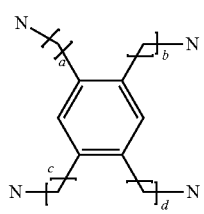

where a, b, c and d, are independently integers 0, 1, 2, 3, 4, 5 or 6

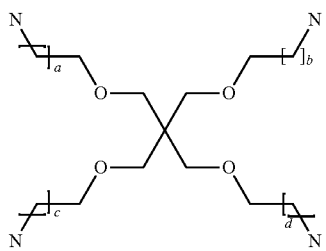

where a, b, c and d, are independently integers 1, 2, 3, 4, 5 or 6

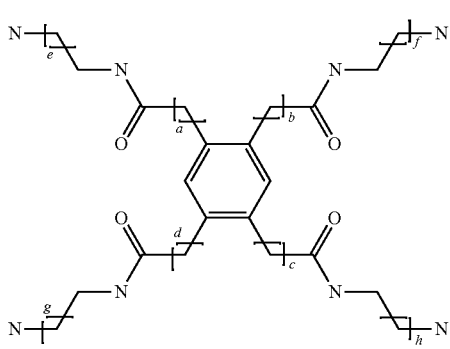

24

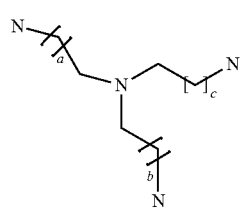

15 where a, b and c, which may be the same or different, are integers of 1 to 2;

where a, b, c and d, are independently integers 0, 1, 2, 3, 4, 5 or 6; and e, f, g and h, are independently integers 1, 2, 3, 4, 5 or 6.

Furthermore, any methylene group of the core may be replaced by a methyleneoxy or ethyleneoxy group provided that this does not result in the formation of a carbonate or carbamate moiety within the core.

In certain embodiments, the core is a triamino compound resulting from reaction of lysine, or a lysine analogue, and a diamino compound selected from the following:

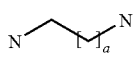

10 where a is an integer 1, 2, 3, 4 or 5;

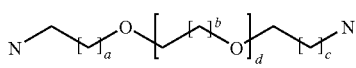

11 where a, b and c, are independently integers of 2 or 3 and d is an integer from 1-30;

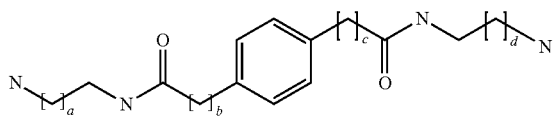

14 where a and d, are independently integers of for 2 and where b and c, are independently integers from 0, 1 or 2.

In particular examples, the core is made up of a diamino compound, such as compound 11 where each of a, b, c and d are 1 (NEOEOEN) and lysine or a lysine analogue, for example, analogue 5, where each of a, b and c are 2 (Su(NPN)$_2$).

In other embodiments, the core is a triamino or tetramino compound selected from the following, either alone or as a reaction product with lysine or a lysine analogue:

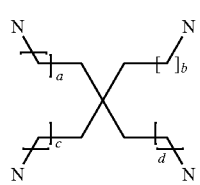

20 where a, b and c, are independently integers 0, 1 or 2; and d, e and f, are independently integers 1 or 2.

or a tetramine compound

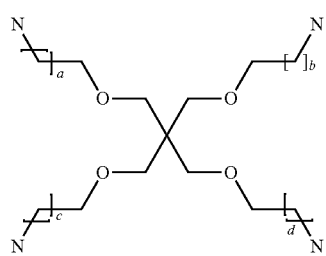

21 where a, b, c and d, are independently integers 0 or 1

23 where a, b, c and d, are independently integers 1 or 2;

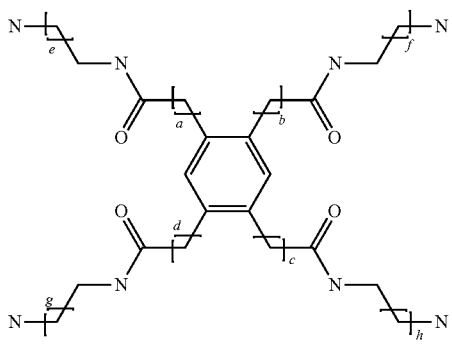

where a, b, c and d, are independently integers 0, 1 or 2; and e, f, g and h, are independently integers 1 or 2.

The preparation of lysine and lysine analogue dendrimer polymers is well known and is described by way of example in U.S. Pat. Nos. 4,289,872 and 4,410,688.

In general, the dendrimer has a core which retains a single reactive site that is preserved (by an appropriate protecting group) whilst the remaining amino sites of the core axe utilised for the addition of building units. The protected reactive site of the core is ultimately used to attach a single entity (first functional moiety) to the core of the macromolecule.

In constructing the dendrimer, it is possible, through the use of amine-protecting groups, to only further react some of the surface amine groups of the building units in a layer or generation, for example by reacting only one of two available amino groups on a building unit, or only one or two of three available amino groups on a building unit, or alternatively, reacting all amino groups on only some of the surface building units, for example every second or third building unit, or two out of three building units. However, in certain embodiments of the invention, each amino group of a building unit in a particular layer or generation is further reacted with a lysine or lysine analogue building unit until the desired number of layers or generations has been constructed. In this manner, for example, when using building units which have two amino groups, the number of building units in a layer is double that of the immediate sub-layer and when using building units which have three amino groups, the number of building units in a layer is three times that of the immediate sub-layer.

A signalling entity is an entity, such as a molecule, or residue thereof, ion or atom, capable of detection, through the generation of a measurable signal.

Examples of suitable signalling entities include:

signal generators, which include anything that results in a detectable and measurable perturbation of the system due to its presence. A signal generator may be defined as an entity which emits a detectable amount of energy in the form of electromagnetic radiation (such as X-rays, ultraviolet (UV) radiation, infrared (IR) radiation and the like) and include phosphorescent and fluorescent entities, and gamma and X-ray emitters, or matter (such as neutrons, positrons, β-particles, α-particles, and the like) and include radionuclides, positron emitters and the like; such as, but not limited to, fluorescing entities, phosphorescence entities and radiation, such as radionuclides, particles and radiation sources, and nucleotides, toxins or drugs labelled with one or more of any of the above, including but not limited to signal generators;

signal reflectors, such as, but not limited to, paramagnetic or magnetic entities, for example, Pe, Gd, or Mn, nitroxyl radicals, NMR shift reagents such as Eu or Pr salts;

signal absorbers may be defined as an entity which absorbs a detectable amount of energy in the form of electromagnetic radiation or matter. Some examples are dyes, contrast agents, electron beam opacifiers, aromatic UV absorber, and boron (which absorbs neutrons). A given entity can be both a signal absorber and a signal generator, i.e. fluorescent or phosphorescent substances can absorb light and emit light; boron absorbs neutrons and emits lunation, and may other such examples, e.g. such as, but not limited to, contrast agents, for example, Gd, Mn or Fe, and electron beam opacifiers such as Pb or Fe.

In certain embodiments of the invention, the signalling entity is a paramagnetic particle.

Paramagnetic particles for use in the contrast agent of the invention are preferably metal ions with atomic numbers 21-29, 42, 44 or 57-83, and more preferably a paramagnetic form of a metal ion with atomic numbers 21-29, 42, 44 or 57-83. These paramagnetic metal ions have unpaired electrons; the number of unpaired electrons in the ion determines the suitability of the ion for use. The paramagnetic metal ion may be selected from the following:

| Atomic N | Metal | Ion | No. of unpaired electrons |
|---|---|---|---|
| 24 | Chromium | $Cr^{3+}$ | 3 |
| 25 | Manganese | $Mn^{2+}$ | 5 |
| 26 | Iron | $Fe^{3+}$ | 5 |
| 27 | Cobalt | $Co^{2+}$ | 3 |
| 29 | Copper | $Cu^{2+}$ | 1 |
| 59 | Praseodymium | $Pr^{3+}$ | 2 |
| 63 | Europium | $Eu^{3+}$ | 6 |
| 64 | Gadolinium | $Gd^{3+}$ | 7 |
| 65 | Terbium | $Tb^{3+}$ and $^{4+}$ | 6 and 7 |
| 66 | Dysprosium | $Dy^{3+}$ | 5 |
| 67 | Holmium | $Ho^{3+}$ | 4 |
| 68 | Erbium | $Er^{3+}$ | 3 |

More preferred paramagnetic ions include $Fe^{3+}$, $Mn^{2+}$ and $Gd^{3+}$. A most preferred paramagnetic ion is $Gd^{3+}$.

As stated above, the paramagnetic metal ions are preferably chelated to the lysine or lysine analogue dendrimer polymer. The main problem with paramagnetic metal ions in their native form is their toxicity. As such, metal ion-chelant complexes should preferably be formed to create a thermodynamically and kinetically stable compound that is much less toxic. Accordingly, the terminal surface groups of the dendrimer may include chelants capable of forming a metal-ion chelant-complex.

In other embodiments of the invention, the signalling entity is a fluorescent agent. Such agents are well known and understood in the art of imaging. Particular agents include the fluorescent moieties dansyl and fluorescein.

Targeted dendrimers of the imaging agent of the invention may further improve the concentration of the agent delivered to the target organ or tissue. Accordingly, as described above, the macromolecules of the invention have at least one targeting molecule attached to the dendrimer, advantageously at the core thereof to provide targeting of the agent. A targeting molecule is a molecule, or residue thereof, which by virtue of its specific binding or interaction with another molecule such as a cell surface receptor, may direct and concentrate the dendrimer at a specific site, such as to specific cell or tissue types. Such targeting molecules are preferably peptides, such as antibodies, optionally in the form of a single chain antibody.

In a preferred embodiment the targeting molecules target receptors or markers expressed on the cell surface. Such targeting molecules may be selected from a group including:

molecules capable of binding to activated leukocytes. Preferably the molecule binds to the Mac-1 receptor molecule, more preferably the activated form thereof. Such a targeting molecule is described in International Application No. PCT/AU2006/001586, the entire disclosure of which is incorporated herein by reference.

molecules capable of binding to activated platelets. A suitable platelet-targeting molecule anti-LIBS antibody has been described in International Application No. PCT/AU2006/00943, the entire disclosures of which are incorporated herein by reference. Alternatively, the platelet-targeting molecule may target the cell adhesion molecule P-selectin.

molecules capable of binding to fibrin Preferably the molecule selectively binds to the amino-terminus of the fibrin beta-chain.

molecules capable of binding to activated endothelial cells. Preferably the molecules bind to cell adhesion molecules, such as the vascular cell adhesion molecule-1 (VCAM-1) and P-selectin.

Accordingly, in this embodiment of the invention, there is provided an imaging agent a macromolecule comprising:

(i) a core moiety having a first amino nitrogen atom for attachment to a first functional moiety and at least two further amino nitrogen atoms for attachment to lysine or lysine analogue building units;

(ii) a first functional moiety attached to the core moiety through the first amino nitrogen atom;

(iii) at least one layer of lysine or lysine analogue building units, the outermost layer having surface amino nitrogen atoms for attachment to one or more second functional moieties, said layers attached to the core moiety through the at least two further amino nitrogen atoms of the core moiety; and (iv) one or more second functional moieties attached to the surface amino nitrogen atoms of the outermost layer of lysine or lysine analogue building units;

wherein
the first and second functional moieties each comprise an agent selected from the group consisting of a targeting molecule and a signalling entity such that the macromolecule has at least one targeting molecule and at least one signalling entity, wherein the targeting molecule is capable of binding to:

(a) activated leukocytes;
(b) activated platelets;
(c) fibrin; or
(d) activated endothelial cells.

Preferably the molecule to be targeted on the activated leukocytes is Mac-1, The Mac-1 targeting molecule described above is preferably a polypeptide including the amino acid sequence motif $DX_1X_2X_3X_4X_5X_6X_7X_8X_9Y$, wherein $X_1$ is S or no amino acid; $X_2$ is independently T, L or F; $X_3$ is independently L or W; $X_4$ is independently A or G; $X_5$ is independently P, F or no amino acid; $X_4$ is Q or no amino acid; $X_7$ is independently I, L or S; $X_8$ is F or Y; and $X_9$ is E or D. The polypeptide or derivative may take a number of forms. However in a most preferred form, the polypeptide or derivative includes the amino acid sequence DSTLAPIFEY, DLWGFQLFDY or DFWGSYDY.

In an alternative form of this embodiment of the invention, the Mac-1 targeting molecule is in the form of a single chain antibody. Preferably the single chain antibody includes one or more of the following regions HCDR1, HCDR2, HCDR3, LINKER, LCDR1, LCDR2, LCDR3. In one embodiment, the HCDR1 is AASGFIFRDYDMD or AASGFSNYGIH or equivalent sequence, the HCDR2 is independently TSSYTIQDAA or VALISYDNGNKKFYA or equivalent sequence, the HCDR3 region is independently DLWGFQLFDY, DFWGSYDY or DSTLAPIFEY or equivalent sequence, the LINKER is independently KLEEGEGSEARV or equivalent sequence, the LCDR1 is independently GGNNIGSKSVH or GGNNIGSTTVH or equivalent sequence, the LCDR2 is independently YDSVRPS or DDNERPS or equivalent sequence, the LCDR3 is independently QVWDSNTDHYV, or QVWDSGSDHVV or equivalent sequence.

In an alternative embodiment of this aspect of the invention the platelet targeting molecule described above has the ability to bind to an activated platelet or a molecule associated with the activated platelet. Typically, this is achieved by binding to a marker on the surface of an activated platelet. There are a number of markers that are predominant on activated platelets including P-selectin, CD40L and activated GPIIb/IIIa. Preferably the targeting molecule targets ligand-induced binding sites (LIBS) on GPIIb/IIIa. In this form, the targeting molecule may include an anti-LIBS antibody.

Alternatively, the platelet targeting molecule may be a molecule that targets a member of the selectin family of cell adhesion molecules. Preferably the selectin family is P-selectin, and may include an anti-P-selectin-antibody.

In a further embodiment, the targeting molecule is capable of binding to activated endothelial cells. Preferably these molecules target cell adhesion molecules, and include molecules to P-selectin as described above. Alternatively, the molecule may be capable of binding to the cell adhesion molecule VCAM-1.

In yet another embodiment, the targeting molecule may target fibrin. The fibrin targeting molecule is preferably in the form of a single chain antibody, more preferably a monoclonal antibody, most preferably anti-fibrin 59D8, which selectively binds to the amino terminus of fibrin-beta chain. This is exposed when thrombin removes fibrinopeptides A and B from intact fibrinogen.

In a preferred embodiment of this aspect of the invention there is provided an imaging agent which comprises a dendrimer polymer as described above, one or a plurality of signalling entities and a first and second targeting molecule. Advantageously the first target molecule is the first functional moiety (attached to the core of the dendrimer) and the second target molecule is attached to the surface of the dendrimer. The first and second targeting molecules may be the same molecules. For example two polypeptides or derivatives thereof capable of specific binding with the high affinity Mac-1 receptor-1. Alternatively, different molecules may be utilised wherein the second targeting molecule binds to a different receptor but on the same target organ or tissue. For example, the second targeting molecule may bind to VCAM-1 expressed on endothelia prone to developing atherosclerosis. As such, the contrast agent would be targeted to activated leukocytes already adhered to activated endothelial cells.

Alternatively, the first targeting molecule may target VCAM-1 and the second targeting molecule may target P-selectin, both of which are expressed on activated endothelial cells. On the basis of these teachings, and the cellular location and tissue distribution of known target molecules, a skilled person would appreciate further combinations.

Binding at multiple sites has been shown to increase the signal intensity of a contrast agent, as a result of a decrease in flexibility of the macromolecule of the contrast agent. In addition, binding of the macromolecule of the contrast agent to multiple target sites includes the following additional benefits:

increases target affinity and provides greater specificity,
slows the rate at which the agent dissociates from the target, thereby increasing the utilization period of the contrast agent.

The macromolecules of the invention may be prepared by a divergent or convergent dendrimer synthesis. Methods for divergent and convergent syntheses are known in the art. In one embodiment, the macromolecule is constructed via a divergent synthesis, wherein the last (surface) layer of building units added may have optionally protected amino groups and/or bear amino groups which have the functional moieties already attached or are modified with a modifier and/or bear a linker moiety for subsequent attachment of a functional moiety.

Alternatively, in a convergent synthesis, dendritic motifs, or wedge, comprising more than a single building unit, can be attached to the core or surface amino groups of a dendrimer. Again, the surface amino groups of a dendritic motif may be optionally protected and/or may already have one or more functional groups attached, and/or are modified with a modifier and/or bear a liker moiety for the functional moiety.

The dendrimer polymer bearing a targeting molecule may be prepared by removing any appropriate amino protecting groups at the core first amino nitrogen or surface amino nitrogen atoms of the dendrimer and attaching a targeting molecule to the deprotected amino atom, optionally via a linker and optionally by modifying the amino nitrogen atom for attachment with a modifier group.

As described above, the functional moieties may be attached to the macromolecule at a selected site of attachment either directly or via a cleavable or non-cleavable linker.

The term "linker" refers herein to any chemical entity which serves to link the functional moieties to the surface or core amino atom. Exemplary linkers contemplated by the present invention include polymers such as polyethylene glycol (PEG), polypropylene glycol, polyaryls, peptides, alkyl and alkenyl chains, and saccharides (mono, oligo and poly).

In particular embodiments, the linker comprises a PEG chain, such as from 1-100 ethyleneoxy repeat units, for example from 2-20 or 2040 repeat units.

Long chain PEG-based groups may be utilised as linker moieties. For example, PEG-peptides may be used in a similar way to conventional peptides, except the PEG moiety provides additional in vivo stability and mass for the carrier. Typically, it is used to conjugate drug to antibody carriers and has the advantage of increasing the distance between antibody and drug while exposing the site of enzymatic cleavage, decrease immunogenicity of the conjugate, increase blood circulation times and increasing the solubility of the complex. Following internalisation of the conjugate and enzymatic release of the active drug (which is not necessarily released as free drug) antiproliferative effects have been observed for Adriamycin and a Duocarmycin derivative.

Where linker moieties are used to connect functional moieties to the core or surface amine of the macromolecules, the reaction between the linker and the functional moiety may be carried out either before, or after, the linker moiety is reacted with the appropriate amine of the dendrimer.

Thus, a linker may be used in a number of ways to attach a first functional moiety to the core. In a first method, the linker may be attached to the core and the first functional moiety is attached to the linker. Alternatively, the linker may be first attached to the functional moiety and then attached to the core. In a third method, both the core and the functional moiety can be attached to a linker or linker component and the two linker moieties subsequently reacted together to provide the linker moiety between the core and the first functional moiety.

Similarly, a linker may be used in various ways to attach a second (or third or fourth) functional moiety to the surface of the dendrimer. The linker may be attached to the surface amino nitrogen atom of the dendrimer and the second (or third or fourth) functional moiety then attached to the linker. Alternatively, the linker may be first attached to the functional moiety, and then attached to the surface amino nitrogen atom. As above, a linker moiety or component thereof can be attached to both the surface amino nitrogen atom and the second (or third or fourth) functional moiety, and the two linkers or components subsequently reacted to provide a linker moiety between the surface and functional moiety.

In addition, linker moieties may be incorporated into the synthesis of the macromolecule according to the present invention, for example between building units. As described above, the linker may be attached to either the surface amino nitrogen atoms, the building unit forming the next layer or both, to ultimately provide a linker between building units.

A reaction which is used to introduce one or more linker moieties onto a dendrimer or dendritic motif (either at the surface or core) is conducted to ensure the complete reaction of all deprotected surface amines of a macromolecule with the linker moieties. Typically this is done by using an excess of the chosen linker moiety.

The linker may be reacted with the deprotected dendritic motif or macromolecule prior to reaction of the linker with the functional moiety. In a further embodiment, the linker attached to the macromolecule may in turn bear a protecting group that requires deprotection to enable reaction with the functional moiety.

Preferably, the amine protecting groups are selected from the group including Boc, CBz, 4-nitrobenzyloxycarbamate (4-$NO_2$—CBz) Fmoc, Dde, $CF_3CO_2$, 2-halo-CBz, Alloc, $Me_3SiEtSO_2$, Troc, o-$NO_2$-$PhSO_2$ and 2,4-dinitrobenzenesulfonylgroups, and preferably from Boc, CBz, 4-nitrobenzyloxycarbamate (4-$NO_2$—CBz), Fmoc 2-halo-CBz, Aloe and $Me_3SiEtSO_2$.

The linker may be cleavable or non cleavable, depending on the requirements of the functional moiety(s) attached. Cleavable linkers may be designed to be enzymatically cleaved, and may for example, be used in macromolecules targeted to tissues expressing those enzymes. Alternatively, an acid labile linker may be preferred such that the compound attached to it is released under acid conditions, such as in hypoxic tissue.

The linker moiety may include repeating units selected to stiffen the backbone thereof, or may be partially cross-linked to stiffen the backbone.

The linker is made cleavable or non-cleavable by the presence of an appropriate stable or labile group in the linker. Examples of suitable cleavable and non-cleavable groups in a linker include:

| Linker type | Summary |
|---|---|
| Amide | Generally used as stable linkers. |
| Hydrazone | Acid labile linkers that are mostly stable at physiological pH have been shown to inhibit the growth of some tumour cells after hydrolysis of the bond to release an anti-tumour drug. |

-continued

| Linker type | Summary |
| --- | --- |
| Oxime | Acid labile linkers that are mostly stable at physiological pH have been shown to inhibit the growth of some tumour cells after hydrolysis of the bond to release an anti-tumour drug. |
| Imine | Acid labile linkers that are mostly stable at physiological pH have been shown to inhibit the growth of some tumour cells after hydrolysis of the bond to release an anti-tumour drug. |
| Ester | The cleavability of esters are strongly related to their structure and number or cleavable sites, where monoesters are more stable that diesters. In general, esters are less stable than amide bonds and more stable than disulfide bonds. Cleavage of orthoesters is dependent on acidic pH. |
| Peptide | A large number of peptide bonds have been investigated as generally non specific enzyme cleavable linkers. Their stability depends largely on the molecules they are attached to and the sequence. |
| disulfide | One of the most unstable linkers available and shows poor stability in circulation. Generally used to facilitate rapid metabolism of toxic species/carriers in target organs. |
| thymidine | While this has not previously been used as a metabolisable linker, thymidine phosphorylase is over expressed in many solid tumours and catalyses the phosphoralytic cleavage of thymidine to thymine and deoxyridose-1-phosphate. | i) Amide Linkers

The nature of an amide bond is important in determining whether the free drug will be released from a conjugate. For instance, conjugation of a drug (e.g. doxorubicin) to a carrier via an amide bond produces a conjugate that is hydrolytically stable and which does not exert any anticancer effects in vitro. A drug bound directly to a carrier via an amide bond will also not be readily cleaved as a free drug, but rather as a drug-amino acid if the carrier is itself degradable. The release of free drug from carriers bound via a direct amide linker will only be achievable in rare circumstances where the drug is itself a peptide-like molecule and the bond between drug and carrier is enzymatically cleavable.

ii) Hydrazone, Oxime and Imine Linkers

Hydrazone, oxime and imine bonds do not require the presence of enzymes to allow cleavage of the drug from the carrier. They are able to be cleaved hydrolytically at the C=N bond in low pH environments such as in the tumour extravascular space or within lysosomes. Commonly used hydrazone, oxime and imine linkers arise from the reaction of a hydrazine, alkoxyamine or amine moieties, respectively, of a linker with a carbonyl (ketone or aldehyde) of a pharmaceutically active moiety. The link may also be modified to slow the rate of hydrolysis by modifying the number of alkyl groups surrounding the C=N bond moiety, or by substitution with electron withdrawing (to increase acid lability) or electron donating (to decrease acid lability) moieties.

iii) Ester Linkers

Both acid labile and metabolisable ester linkers can be made. Orthoesters have been used to conjugate PEG to lipids which bind anionic membrane carriers. The stability of the conjugate in acidic conditions (pH 4-6) depends on the structure of the ester or orthoester linker. In general, α-methoxy-ω-{N-(2-octadecyloxy-[1,3]dioxolan-4-yl)methylamido}-polyethyleneglycol$_{110}$ shows good stability at both pH 4 and 5, α-methoxy-ω-{N-(2-cholesteryloxy-[1,3]dioxolan-4-yl)methylamido}-polyethyleneglycol$_{110}$ is very stable at pH 5 but moderately less stable at pH 4, α-methoxy-ω-{N-(2-methyl-s-octadecyloxy-[1,3]dioxan-5-yl)-amido}-polyethyleneglycol$_{110}$ and α-methoxy-ω-{N-2-(3-hydroxypropyl-cholesterylcarbarnate)-2-methyl-[1,3]dioxan-5-yl-amido}-polyethyleneglycol$_{110}$ are not stable. In terms of simple ester conjugation to small molecules, diester functionalities provide more sites for metabolic cleavage compared with monoesters which are more stable than disulfides but less stable than amide bonds.

iv) Peptide Linkers

Peptide linkers are by far the most versatile of all cleavable linkers in that many different combinations of amino acids can be used to control the rate of cleavage and the cleavage enzyme. However, these linkers have two problems associated with their use as conjugates for drug and carrier, 1) they are generally cleavable by non specific peptidases throughout the body and may therefore result in non-specific drug toxicity at non-tumour distribution sites and 2) cleavage may occur at a site within the linker that results in an amino acid remaining bound to the drug molecule. This may hinder the chemotherapeutic effect of the drug molecule. Alternatively, the bound amino acid may not alter the pharmacological effects of the drug but may affect its pharmacokinetics. However, these cleavage effects may be controlled by choosing an appropriate amino acid in the peptide linker that is bound directly to the drug molecule, e.g. proline.

Generally, cathepsin B cleavable linkers have been designed to be cleaved following endocytosis of the drug conjugate via the lysosome system, as cathepsin is located in lysosomes and not free in the cytosol. Endocytosis is generally initiated following binding of the carrier (which is usually an antibody directed against a cancer specific cell surface receptor or ligand for a cancer specific cell surface receptor) to the cell membrane.

Non-specific proteases (i.e. proteases that are not specific for a particular peptide sequence) may cleave a drug from a PEGylated macromolecule after it has undergone sufficient extravasation and accumulation in tumour tissue.

The following guidelines about the rate of peptide cleavage apply, where a>b indicates that the rate of cleavage of a is greater than the rate of cleavage for b. For peptide sequences used as linkers between an active pharmaceutical and the dendrimer terminal nitrogens: terminal Cys>no terminal Cys Gly>terminal Gly=terminal, Gly Phe Gly>terminal GlyGlyGly and terminal GlyGlyGlyPhe=terminal GlyProGly.

Note: CysGly bonds are reduced by GSH. GlyGlyGly bonds are generally very stable relative to other peptide bonds. The cleavage of dipeptides is generally specific to particular proteases and may be controlled based on the expression of various proteases contained within tumour cells.

v) Disulfide Linkers

Disulfide linkers are the most unstable linkers currently used and undergo rapid reductive cleavage in vitro. Their in vivo stability is generally higher, however, than their in vitro stability. They may be formed via disulfide linkages between sulphur containing amino acids or at non peptide based disulfide bonds. They also show greater reactivity with other nucleophilic thiols in the body and hence show rapid plasma clearance.

General Summary of Linker Cleavability

In circulation, the order of linker cleavabilities is as follows;

Disulfide>long chained peptides≥esters>hydrazones≥etrapeptides (GlyGlyGlyPhe)=tripeptides (GlyPheGly>GlyGlyGly=GlyProGly)≈ or >dipeptides (AlaVal, AlaPro, GlyPro, PheLeu, Val-Cys)>glutaraldehyde=amide.

The stability of various linkers is based on the groups to which they are conjugated (i.e. accessibility of the enzymes to the linker), the behaviour of the conjugate at the site of required activity (i.e. cellular uptake or extracellular accumulation) and the nature of the conjugate (i.e. ester vs. amide). The in vivo behaviour of the disulfide conjugates with the current system is expected to be relatively unpredictable. While long chained peptides are more easily assessed by proteases for rapid cleavage, they may be cleaved too rapidly and at non specific sites, resulting in release of a pharmaceutical active-peptide/amino acid species which may not be biologically active.

Cleavage of a C=N based linker (hydrazone, oxime or imine), ester or peptide conjugates will occur at least over several days which allows the conjugates to accumulate in tumour tissue. Each has its advantages, but ester or hydrazone linkers may be preferred. An ester bond linking a pharmaceutical active to the macromolecule provides a bond that is rapidly cleaved, and though this may not be specific to the target site, cleavage results in the release of free a pharmaceutical active. Hydrazone bonds produce conjugates are more stable in the general circulation than esters and are cleaved with greater specificity at the tumour site via hydrolysis at the C=N bond. However, the pharmaceutical active molecule may need to be modified to allow hydrazone formation either by incorporation of a carbonyl or hydrazine moiety.

In some embodiments, the linker moiety may include two reactive groups, F' and Y', which are connected by one or more carbons or heteroatoms, preferably by a hydrocarbon backbone. The reactive group F' may be activated to react with reactive amine moieties like those on the core, or the surface or subsurface layer of the dendritic motif. Typically the reactive group F' is a carboxylate group or residue thereof. The other functional moiety, Y', is either an amine comprising a protecting group, or it is selected such that it has a specific reactivity that is complementary to a reactive group of a desired functional moiety that is to be attached to the core, or the surface layer or subsurface layer of a dendritic motif. Typical examples of Y' include amine, hydroxyl, thiol, alkenyl or alkynyl, nitrile, halide, carboxylate or azido groups.

In addition to the linkers described above, photocleavable linkers may be used with the present invention. For example, heterobifunctional, photocleavable linkers may be used. Heterobifunctional, photocleavable linkers may be either water or organic soluble. They contain an activated ester that may react with amines or alcohols and an epoxide that may react with a thiol group. Between the ester and epoxide groups is a 3,4-dimethoxy-6-nitrophenyl photoisomerisation group, which, when exposed to near-ultraviolet light (365 nm), releases the amine or alcohol in intact form. Thus, the pharmaceutically active component, when linked to the macromolecule using such linkers, may be released in biologically active or activatable form through exposure of the target area to near-ultraviolet light.

In further embodiments, preparation of the macromolecule may further include the step of modifying the amine group and/or linker and/or functional moiety to facilitate ligation of the functional moiety to the amine, either directly or via the cleavable or non-cleavable linker.

Thus, the amine group at the surface or core of the macromolecule can be modified by a modifier group to facilitate attachment to the linker or functional moiety. Alternatively, or in addition, the linker may be modified to facilitate attachment to the surface or core amine group.

The terminus of the linker for attachment to the functional moiety may be modified by a modifier group to facilitate attachment to the functional moiety. Alternatively, or in addition, the functional group may be modified by a modifier group to facilitate attachment to the linker or directly to the surface or core amine group.

In a particular embodiment, the first amino nitrogen atom of the core and/or a linker used to attach the first functional moiety and/or the first functional moiety is further modified to facilitate attachment of the first functional moiety to the core.

The amino (surface or core) moiety and/or linker and/or functional moiety may be modified to allow for the ligation either of the functional moiety, to the amino atom, via the linker by derivatisation with a group that includes a chemical moiety selected from: a haloacetamide, a maleimide or other thiol reactive moiety, a reactable thiol or exchangeable disulfide moiety, an aliphatic or aromatic aldehyde, a ketone, an alkoxyamine, a hydrazine, an azide, an alkyne, an oligohistidine array and any peptide array, a nitrilotriacetic acid group, any carboxylate or reactive residue thereof (such as activated esters); any chemical moiety capable of reacting with an organic halide such as an organostannyl group, an acrylate, a boronic acid (or ester) and organic alkynes via metal catalysed coupling reactions, namely Stille, Heck, Suzuki and Sonogashira respectively, any moiety capable of enzymatic ligation (e.g. through the use of a transglutaminase), any moiety capable of native chemical ligation. Methods for derivatisation to incorporate the modifier are known in the art.

More preferably, the chemical modifier may be selected from the following (i) Maleimide

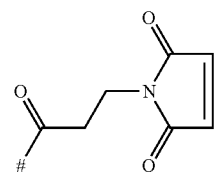

(ii) Haloacetamide (X=Cl, Br, I)

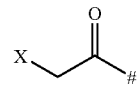

(iii) Hydrazide

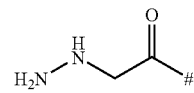

(iv) Alkoxyamine

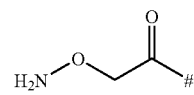

(V) 3-(2-Pyridyldithiothio)propionate

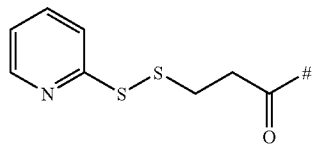

In certain embodiments, the surface or core amine may be modified to allow for the ligation of the functional moiety by derivatisation with a group that includes a chemical moiety selected from: haloacetamide, maleimide or other thiol reactive moiety, a reactable thiol or exchangeable disulfide moiety, aldehyde, ketone, an alkoxyamine moiety, hydrazine, azide, alkyne, oligohistidine array, nitrilotriacetic acid motif.

In a preferred method, the protecting group of the selected amine, such as the core amine, is removed, and the amine is reacted with a haloacetic acid derivative, or a maleimide derivative such as 3-maleimidopropionic acid or 4-maleimidobutyric acid under conditions where the amide bond is formed. General methods for the coupling of thiol containing peptides and proteins to such thiol active groups are described in Hermanson, G. T. Bioconjugate Techniques (Academic Press 1996) and the references cited therein.

General methods for the covalent coupling of macromolecules to molecules such as peptides and antibodies are within the level of skill in the art. Such methods are described in Hermanson, G. T, Bioconjugate Techniques (Academic Press 1996) and the references cited therein, Blatter et al, *Biochem.*, 24; 1517 (1985) and Jue et al, *Biochem.*, 17:5399 (1978). Methods for the ligation of peptides or proteins containing adjacent histidine residues with macromolecules or solid supports containing the nitrilotriacetic acid motif through complexation with nickel are described in Hochuli et al *J. Chromatogr.* 1987 411 177, Sigel et al *Anal. Chem.* 1996 68 490 and Gershon et al *J. Immunol. Meth.* 1995 183 65. The references cited above are incorporated herein by reference in their entirety.

Preferably the targeting molecule is ligated to the dendrimer polymer, via the chemical moiety, by a covalent bond formation or metal complexation.

Preferably, the targeting molecule is a polypeptide or polypeptide in the form of an antibody.

In a preferred embodiment of the invention, the targeting molecule, preferably a peptide or peptide in the form of an antibody, is synthesised to have multiple adjacent histidine residues (poly-histidine motif) at either the N or C terminus, a cysteine tag, or a combination thereof, to facilitate the reaction with the deprotected dendrimer.

Targeting peptides and antibodies may be expressed fused to an N or C terminal, preferably N terminal, poly-histidine motif. The terminal poly-histidine motif may be utilised to conjugate the targeting peptide to the dendrimer of the contrast agent of the invention through a Nickel complex, wherein the Nickel Ions are present as terminal surface groups on the dendrimer or on the ends of linkers extending from the dendrimer, in complex with nitrilotriacetic acid moieties. Alternatively, the poly-histidine motif may be utilised for one-step purification using Nickel affinity resins and optionally removed from the purified molecule by the inclusion of an enterokinase or endopeptidase cleavage recognition site. Such purification methods will be known to the skilled person.

More preferably the targeting polypeptide or antibody may be expressed fused to a N or C terminal, preferably N terminal, cysteine tail. Cysteine contains a highly nucleophilic thiol group which may be utilised in the presence of thiol-specific reactive groups, such as chloro, bromo or iodoacetamide groups or the maleimide moiety to form a thioether linkage coupling the targeting polypeptide or antibody to the dendrimer. These thiol reactive groups would be provided in the dendrimer material through reaction of appropriated derivatising agents such as haloacetyl chlorides or maleimide derivatives of glycine or 3-aminopropionic acid, with one or more selectively deprotected terminal surface amines of the dendrimer species.

The targeting polypeptide or antibody may also be expressed with a combination of cysteine and histidine tails. The cysteine and histidine tail may either be expressed, each at the opposite end to the other, (e.g. N terminal cysteine tail and a C terminal histidine tail), or both at the N or C terminal.

Preferably, the paramagnetic metal ions are attached to the chelant moieties on the dendrimer prior to the attachment of the targeting molecule, thereby minimising non-specific binding of the paramagnetic metal ions to the targeting molecule and avoiding conditions that may denature the molecule. However chelation of the paramagnetic particles to a dendrimer-targeting molecule complex is also contemplated, followed by purification to remove excess un-chelated paramagnetic particles.

i) Suitable Chelants

Suitable chelants include but are not limited to polyaminopolycarboxylic acid (PAPCA) chelants, particularly diethylenetriamine pentacetic acid (DTPA) and derivatives thereof. Other alternatives include 1,4,7-triazacyclononane; 1,4,7,10-tetraazacyclododecane (Cyclen) and derivatives thereof; 1,4,7,10-tetraazacyclododecane-1,7-bis(acetic acid ter-bu-ester) (DO2A-t-bu-ester); 1,4,7,10-tetraazacyclododecane-1,4,7-tris(acetic acid, t-bu-ester) (DO3a-t-bu-ester); 1,4,7-tris(tert-butoxycarbonyl)-1,4,7-tetraazacyclododecane (DO3-t-BOC); 1,4,7,10-tetraazocyclododecane-N,N',N'''-triacetic acide (DO3A); 1,4,7,10-tetraazacyclododecane-1,4,7,10-tetraacetic acid (DOTA) and derivatives thereof; 1,4,7,10-tetraazacyclododecane-1,4,7,10-tetrakis(methylene phosphonic acid) (DOTP); 1,4,7,10-tetraazacyclododecane-1,4,7,10-a,a',a'',a'''-tetrakis (methylacetic acid) (DOTMA); ethylenediamine-tetra-acetic acid (EDTA); trans-1,2-diaminocyclohexane-N,N',N'',N'''-tetraacetic acid (CDTA); 1,8-dioxo-triethylene-tetraamine-N,N',N'',N'''-tetraacetic acid (DTTA); 1-oxa-4,7,10-triazacyclododecantriaacetic acid (DOXA); 4,10,16-trioxacyclooctadecane-N,N',N''-triacetic acid (TTTA); 1,4,8,11-tetraazacyclotetradecane-1,4,8,11-tetraacetic acid (TETA); ethylenebis(2-hydroxy-phenylglycine)(EHPG) and derivatives thereof, including 5-Cl-EHPG, 5-Br-EHPG, 5-Me-EHPG, 5-t-Bu-EHPG, and 5-sec-Bu-ERPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which comprise at least 3 carbon atoms, more preferably at least 6, and comprise at least two heteroatoms (O and/or N), said macrocyclic compounds may comprise one ring, or two or three rings joined together at the heteroatom ring elements, e.g., benzo-DOTA, dibenzo-DOTA and benzo-NOTA, where NOTA is 1,4-triazacyclononane-N,N',N''-triacetic acid, benzo-TETA, benzo-DOTMA, benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); and derivatives of 1,5,10-N,N',N''-tris(2,3-dihydroxybenzoyl)aminomethylbenzene (MECAM).

DTPA in particular refers to a structure of any one of Formulae (I) to (IV):

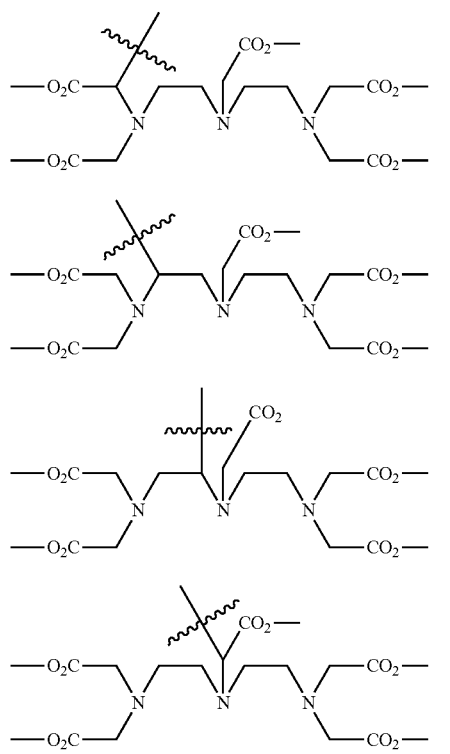

Preferably the dendrimer of the contrast agent has paramagnetic Gd chelates such as gadolinium diethylenetriaminepentaacetic acid (GdDTPA), gadolinium tetraamine 1,4,7,10-tetraazacyclododecane-N,N',N'',N'''-tetraacetic acid (GdDOTA) and gadolinium 1,4,7,10-tctraazacyclododecarte-1,4,7-triacetic acid (GdDO3A). It is known in the art that other metals may be substituted for Gd(III) in certain applications. A preferred chelator for use in the invention is DTPA. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, all of which are herein incorporated by reference.

The number of chelant moieties on the surface of each dendrimer is dependent on the valency of the core from which the dendrimer is assembled, and on the number of layers of lysine building units used in the assembly of the dendrimer. For example, a dendrimer of 1 layer of lysine building units on a divalent core has capacity to bear 4 chelant moieties; a dendrimer of 2 layers of lysine building units on a divalent core has capacity to bearing 8 chelant moieties; a dendrimer of 3 layers of lysine building units on a divalent core has capacity to bear 16 chelant moieties and a dendrimer of 4 layers of lysine building units on a divalent core has capacity to bear 32 chelant moieties.

ii) Attachment of Chelants to Lysine Dendrimer Polymer—Direct

The attachment of chelant moieties to the lysine dendrimer polymer of the invention may be achieved in a number of ways. For example, the mixed anhydride procedure of Krejcarek et al. (Biochemical and Biophysical Research Communications 77:581 (1977)), the cyclic anhydride procedure of Hnatowich et al. (see Science 220: 613 (1983) and elsewhere), the backbone derivatisation procedure of Meares et at, (see Nal. Biochem. 142: 68 (1984) and elsewhere—this is a technique used by Schering in EP-A-331616 to produce site specific polychelates for use as MRI or X-ray contrast agents), and the linker molecule procedure used for example by Amersham (see WO-A-85/05554) and Nycomed (see EP-A-186947 and elsewhere) to produce paramagnetic metal ion chelates of bifunctional chelants for use as MRI contrast agents.

The macrocyclic chelant moieties may be conjugated to the terminal surface amine groups on the dendrimer or the terminal surface amine groups of the dendrimer may be modified to provide terminal carboxylates, alcohols, or thiolates, etc. The linkage between the dendrimer amine groups and the chelant moiety is preferably via an amide bond, the amide nitrogen deriving from the dendrimer and the amide carbonyl group deriving from a carboxyl or carboxyl derivative functionality on the macrocyclic chelant. Preferably the macrocyclic chelant is a PAPCA, more preferably DTPA, and most preferably the carboxyl or carboxyl derivative functionality is attached to the chelant.

The chelant moieties in the dendrimers of the current invention preferably derive from chelants which have a reactive carboxyl or amine group which is not essential for metal coordination bonding. The reactive group may be one of the groups which in the free chelant can function as a metal coordinating group so long as the conjugated chelant moiety retains the ability to complex metal ions. Alternatively the reactive group can be a substituent on a side chain of the chelant or on a backbone carbon.

The macrocyclic chelants may also be conjugated to the dendrimer through a non-coordinating primary amine group. Macrocyclic chelants having a non-coordinating primary amine group include primary amine side-chain-derivatized DOTA macrocycles, primary amine-derivatized DO3A, and primary amine-derivatized hexaaza and octaaza macrocycles and macrobicycles (the ITAMs, sepulchrates and sarcophagines) as well as the broad class of derivatised crown ether cryptates.

The non-coordinating primary amine group on these chelants may be reacted with a haloacetylhalide under wellknown conditions to form a haloacetamide. The haloacetamide may react with a primary amine of the dendrimer to form a stable amide linkage between the chelant and the dendrimer. The haloacetylhalide method described in De Riemer et al, J. Labelled Compd. Radiopharm, 18:1517 (1981) can be used to join amine-containing chelants to the dendrimer.

Amine groups on a macrocyclic chelant may also be reacted with phosgene to generate a reactive isocyanate group, or with thiophosgene to generate a reactive isothiocyanate group. Those groups can react with a primary amine of the dendrimer surface groups to form a stable urea or more stable thiourea linkage, respectively, between the ligand and the dendrimer. Gansow, Inorg. Chimica Acta 91:213 (1984) and Moi et al, J. Amer. Chem. Soc. 110; 6266 (1988) describe methods of linking chelants to proteins having an amine group through formation of the isocyanate or isothiocyanate moieties using the phosgene or thiophosgene methods, respectively. See also Desreux, Inorg. Chem. 19:1319 (1980); Bryden et al, Anal. Chem 53:1418 (1981); Delgardo et al, Talanta 29:915 (1982).

For macrocycles with a pendant carboxylate, including but not limited to DOTA, TETA, TRITA (1,4,7,10-tetraazacyclotridecanetetraacetic acid) and NOTA, one of the carboxylates can be activated to react with a primary amine group of the dendrimer.

Methods of forming a reactive entity from a carboxylate group have been described above. Such reaction sequences give rise to a dendrimer multiply substituted with the macrocyclic chelant moieties through stable amide linkages. In a preferred method only one of the multiple carboxylate moieties of the chelate are activated for amide bond with the dendrimer, and this is done through the use of a single equivalent of carboxylic acid activating reagent per chelant, and use of a sufficient excess of chelant relative to dendrimer amine to ensure complete reaction. Purification of the dendrimer-chelant construct is achieved using size exclusion chromatography or ultrafiltration techniques.

iii) Attachment of Chelants to Dendrimer—Indirect

As an alternative, the dendrimer may be linked to the macrocyclic chelant moiety via a linker group attached to the macrocyclic chelant.

The linker moiety may be any small subunit comprising 1 to 30 carbon atoms covalently connected by single or multiple bonds wherein up to 10 of the carbon atoms may be substituted with O, N, S, F, Cl, Br, H or I. The linker functions to connect the chelants to the dendrimer. Examples of linkers include linear or branched alkanes, alkenes, or alkynes optionally substituted with functional groups such as, carbonyl, ether, amide, amine, urea, thioether, aryl, phosphate, sulphonamide and the like. The preferred linkers of certain embodiments embody two or more functional chemical groups, one of which is attached to the dendrimer and the others of which are attached to the chelant. Alternatively, the chelants may be linked with a his amine, bis epoxide, diol, diacid or a difunctionalised PEG linker moiety.

Incorporation of Paramagnetic Particles

Methods of complexing the paramagnetic particles, preferably metal ions, with chelants are within the level of skill in the art. Each of the metals used may be incorporated into a macrocyclic chelant moiety by one of three general methods: direct incorporation, template synthesis and/or transmetallation. Direct incorporation is preferred.

The metal ions Pe(III), Cr(III), Mn(II), Hg(II), Pb(II), Bi(III) and the lanthanides may be directly incorporated into PAPCA by the following general procedure. A water-soluble form of the metal, generally an inorganic salt, is dissolved in an appropriate volume of distilled, deionized water. Preferably, such salts are selected so as not to interfere with the binding of the metal ion with the chelant. The pH of the solution will be below 7. An aqueous solution containing an equimolar amount of the polychelants is added to the metal solution at room temperature while stirring. The pH of the mixture is raised slowly by addition of base, typically 0.1 M NaOH, until the donor groups of the polychelants are deprotonated, generally in the pH range of 7 to 9, depending on the chelant moieties. Particular care must be taken with the lanthanide ions to maintain the pH below 8 to avoid precipitation of the metal hydroxide. Metal incorporation into DOTA derived and related macrocyclic chelant moieties will normally be a slow process, as described in the references cited below.

Choppin et al, J. Inorg. Nucl. Chem., 33:127 (1971), Margerum, Rec. Chem. Prog., 24:237 (1973) and D'Olieslager et al, J. Inorg. Nuel. Chem, 35:4255 (1973) describe direct incorporation of the lanthanides into PAPCAs. Margerstadt, Mag. Res. Ivied., 3:808 (1986) and WO-A-87/06229 describe incorporation of Gd(III) into DOTA. The above references are incorporated herein by reference in their entirety.

In yet another aspect Of the invention, there is provided a single-vial or multi-vial kit that contains all of the components needed to prepare the contrast agents of the invention, together with instructions.

Use of Contrast Agents

In a further aspect of the invention, there is provided a method for imaging, such as magnetic resonance imaging, of a cellular target in a mammal, the method including the steps of (a) administering to a mammal an imaging agent according to the invention;

(b) allowing the imaging agent to bind to the cellular target; and (c) imaging the mammal to generate an image.

Preferably signalling entities of the agent comprise the paramagnetic particles, which may include metal ions, more preferably Gd ions, chelated to the dendrimer of the contrast agent.

In a preferred embodiment, the imaging of a cellular target is indicative of a disease or condition.

In one embodiment, the dendrimer polymer of the contrast agent may be suitable for the use for the detection of activated endothelial cells, wherein the targeting molecules as described above and herein in further detail, may be selected from the group including molecules capable of binding to endothelial adhesion molecules, such as the activated form of the Mac-1 receptor molecule, or to VCAM-1 or to P-selectin. Accordingly, the contrast agent may be suitable for use for the diagnosis of early stage atheroscleroses as described below. Detection of fibrin may also be utilised for this purpose.

In another embodiment, the contrast agent may be suitable for use for the detection of activated platelets wherein the targeting molecule may be either an anti-LIBS antibody or a molecule capable of binding to P-selectin, as described above and herein in further detail. Accordingly, the dendrimer polymer of the contrast agent may be suitable for the diagnosis of blood coagulation disorders, particularly at an early stage.

MRI contrast agents as described herein may be used in like manner to those of existing contrast agents.

In a still further aspect of the invention, there is provided a pharmaceutical composition including
a macromolecule according to the invention, and
a pharmaceutically acceptable excipient, carrier or adjuvant therefor.

Suitable pharmaceutical excipients include stabilizers, antioxidants, osmolality adjusting agents, buffers, and pH adjusting agents. Suitable additives include physiologically biocompatible buffers (e.g., tromethamine hydrochloride), or additions (e.g., 1 to 50 mole percent) of calcium or sodium salts (for example, calcium chloride, calcium ascorbate, calcium gluconate or calcium lactate). The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc.

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiment's of the invention.

The compositions may be formulated in accordance with routine procedures as a pharmaceutical composition adapted for intravenous administration to human beings or in animal model systems. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection" or saline. Where the composition is to be administered by injection, an ampule of sterile water for injection or saline may be provided so that the ingredients may be mixed prior to administration.

The composition is preferably administered to the patient in the form of an injectable composition. The method of administering the composition is preferably parenterally. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection; subcutaneous injection or deposition including subcutaneous infusion (such as by osmotic pumps); and direct application to tissue, for example by a catheter or other placement device (e.g. a suppository or an implant comprising a porous, non-porous, or gelatinous material, a sialastic membrane, or a fiber).

Pharmaceutical compositions of this invention can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

The methods of using the MRI contrast agent will now be described in relation to two specific applications.

Early-Stage Diagnosis of Atherosclerosis

Atherosclerosis is the most prominent coronary artery disease which causes progressive and chronic narrowing of the arterial lumen due to lesions initiated as focal thickenings of the inner most layer of the artery. The lipid-rich atherosclerotic lesions consist of vascular, endothelial and smooth muscle cells, fibroblasts as well as leukocyte infiltrates which define atherosclerosis as a chronic inflammatory disease. Leukocyte recruitment is a critical step in the initiation of atherosclerosis.

The development of an atherosclerotic lesion requires a complex interplay between leukocytes (e.g. monocytes, macrophages and neutrophils), endothelial cells, vascular smooth muscle cells, growth factors and cytokines. Detection of one or more molecules on the surface of any one of these components may be useful in the early stage diagnosis of atherosclerosis. One of the first and most crucial events in this development is the adhesion of leukocytes to the endothelial lining and subsequent diapedesis. Adhesion is mediated by interaction with adhesion molecules expressed on endothelial cells, particularly activated endothelial cells.

More specifically, adhesion may be mediated by interaction between intercellular adhesion molecule-1 (ICAM-1) expressed on endothelial cells and the $\beta_2$-integrin receptor Mac-1 expressed on leukocytes. Generally, Mac-1 is only able to participate in inflammatory pathways when in the activated form. Accordingly, it is valuable to be able to detect leukocyte adhesion to vessel walls as an early diagnosis of atherosclerosis.

Another important molecule is VCAM-1. VCAM-1 is an immunoglobulin-like adhesion molecule expressed on endothelia, epithelial and dendritic cells and macrophages. VCAM-1 can mediate both rolling-type adhesion and firm adhesion, depending on the avidity status of $\alpha 4 \beta 1$ integrin VLA-4. Although it is structurally similar to ICAM-1 and other endothelial adhesion molecules, VCAM-1's pattern of regulation is unique. VCAM-1 is not expressed under baseline conditions but is rapidly induced by atherosclerotic conditions including in early lesions, resulting in stronger adhesion and migration of monocytes and lymphocytes.

Also involved in P-selectin. P-selectin is a member of the selectin family of cell adhesion molecules. It is expressed on stimulated endothelial cells and mediates leukocyte rolling on stimulated endothelial cells.

To this effect, the dendrimers of the contrast agents of the current invention may be targeted to such inflammatory lesions by a molecule as herein described that is capable of binding to the activated form of the Mac-1 receptor molecule, the VCAM-1 adhesion molecule or the P-selectin adhesion molecule.

Given the biological activity of the polypeptide or derivatives described above, the contrast agent may be useful in methods of medical treatment and diagnosis.

Accordingly, the invention further provides a method for detecting the presence, absence or level of activated Mac-1, the VCAM-1 adhesion molecule or the P-selectin adhesion molecule, in a subject or a test article, the method including exposing the subject, or a biological sample of the subject or the test article, to a contrast agent or composition thereof, wherein the targeting molecule is capable of specific binding with the high affinity Mac-1 receptor-1, VCAM-1 or P-selectin respectively.

The presence of activated Mac-1, VCAM-1 or P-selectin in particular is indicative of atherosclerosis. Accordingly, the present invention provides a method of diagnosing early stage atherosclerosis including the steps of administering a contrast agent to a mammal wherein the contrast agent includes a targeting molecule capable of binding to the activated form of the Mac-1 receptor molecule;

allowing the MRI contrast agent to bind to the cellular target; and imaging the mammal to generate a MR image.

In another embodiment the targeting molecule is capable of binding to VCAM-1, and in yet another embodiment the targeting molecule is capable of binding to P-selectin.

Preferably the paramagnetic particles of the contrast agent include metal ions, more preferably Gd ions, chelated to the dendrimer of the contrast agent.

In yet another embodiment the invention provides a method for detecting the presence, absence or level of fibrin in a subject or a test article, the method including exposing the subject, or a biological sample of the subject or the test article, to a contrast agent or composition thereof, wherein the targeting molecule is capable of specific binding with fibrin.

Fibrin may form part of an atherosclerotic plaque. Accordingly the present invention provides a method of diagnosing early stage atherosclerosis including the steps of administering a contrast agent to a mammal wherein the contrast agent includes a targeting molecule capable of binding to fibrin;

allowing the MRI contrast agent to bind to the cellular target; and imaging the mammal to generate a MR image.

Preferably the targeting molecule is a single chain monoclonal antibody which selectively binds the amino-terminus of the fibrin beta-chin.

Detection of Inflammatory Processes in General

Mac-1 is involved in various pathophysiological processes like inflammation, atherosclerosis and ischemia and thus its activation-state and expression levels are altered in multiple diseases including myocardial infarction, sepsis, rheumatoid arthritis. Mac-1 expression has been shown to correlate with the risk of restenosis after coronary angioplasty, to correlate with procoagulant activity after angioplasty in patients with acute myocardial infarction and to reflect the therapeutic effects of anti-platelet agents on monocyte activation after coronary stent implantation. Overall, in immune response related diseases and in inflammation in general, activation-specific, anti-Mac-1 scFvs may provide new diagnostic opportunities.

Detection of Activated Platelets

Clotting must be very strictly regulated because even one inappropriate clot can have fatal consequences. Indeed, blood clots are the leading cause of strokes and heart attack, the two major causes of human death. Current therapeutic anticoagulants are also a major source of mortality and morbidity, caused by limitations in efficacy and even more so by bleeding complications. As such, it is desirable to be able to detect the formation of thrombus at an early stage in order to minimise the need and/or extent of treatment with anticoagulants.

The process of blood clotting and then the subsequent dissolution of the clot, following repair of the injured tissue, is termed hemostasis. The initial phase of the process is vascular constriction. This limits the flow of blood to the area of injury. Next, platelets become activated by thrombin and aggregate at the site of injury, forming a temporary, loose platelet plug. The protein fibrinogen is primarily responsible for stimulating platelet clumping. Platelets clump by binding to collagen that becomes exposed following rupture of the endothelial lining of vessels. Upon activation, platelets release adenosine-5'-diphosphate, ADP and TXA2 (which activate additional platelets), serotonin, phospholipids, lipoproteins, and other proteins important for the coagulation cascade.

There are a number of markers that are predominant on activated platelets including P-selectin, CD40L and activated GPIIb/IIIa. The marker may be one that takes an inactive and an active form such that one form is found to predominate over the other in activated platelets, as compared with other components of the coagulation system. One of the most abundantly expressed molecules on the platelet surface is the glycoprotein receptor (GP) IIb/IIIa (CD41/CD61). This receptor belongs to the adhesion molecule family of integrins and is also termed $\alpha_{IIb}\beta_3$. Integrins consist of two non-covalently linked subunits that undergo a conformational change from a low affinity to a high affinity receptor in respect to the binding of the GPIIb/IIIa ligand fibrinogen. Besides the exposure of the ligand binding pocket, this conformational change also induces the exposure of so-called ligand-induced binding sites (LIBS) on GPIIb/IIIa. Since these binding sites are specific for the activated and/or ligand bound GP IIb/IIIa receptor and since GPIIb/IIIa is highly abundant with around 60,000 to 80,000 molecules on the surface of each platelet, the prerequisites for an epitope to be used for clot targeting are very unique.

The contrast agent may be suitable for use in a method of diagnosis or prognosis of a coagulation disorder in a subject, the method including the detection of activated platelets in a blood vessel of the subject.

The invention provides a method of detecting blood coagulation disorders including the steps of
administering a contrast agent to a mammal wherein the contrast agent includes a targeting molecule being an anti-LIBS antibody;
allowing the MRI contrast agent to bind to the cellular target; and
imaging the mammal to generate a MR image.

In another embodiment the targeting molecule is capable of binding to P-selectin. Preferably, the molecule is a single chain antibody.

Preferably the blood coagulation disorder involves activated platelets.

Preferably the paramagnetic particles of the contrast agent include metal ions, more preferably Gd ions, chelated to the dendrimer of the contrast agent.

The detection of activated platelets will provide the clinician with a relevant marker useful in a number of medical applications. One application is to image activated platelets found on ruptured coronary plaques or those plaques that are prone to rupture. This will allow for an early non-invasive diagnosis of acute coronary syndromes with following prophylactic implantation of stents into relevant lesions possible. This is of special clinical interest as coronary angiography only provides information about the vessel lumen, but not about the morphology of the vessel wall itself. Thus, possible ruptured or rupture-prone plaques are not detected with coronary angiography.

A further application includes use of the single-chain antibodies and methods described in International Application No. PCT/AU2006/00943 (herein incorporated) as well as molecules capable of binding to P-selectin to detect any accumulation of activated platelets, for example in pulmonary or peripheral embolism, or on ruptured atherosclerotic plaques in peripheral or cerebral arteries. These lesions could be detected early in the disease process and selectively treated.

The skilled person will understand that the single-chain antibodies and methods described herein may be useful in identifying individuals having a predisposition to a coagulation disorder, without necessarily demonstrating as a clinically recognizable sign or symptom of a coagulation disorder.

In a preferred form of the method, the step of detecting an activated platelet includes the use of a single-chain antibody. Preferably the single-chain antibody is the same as, or similar to, the anti-LIBS antibody or a P-selectin antibody. Indeed, the skilled person will understand that it may be possible to use a fragment of the single-chain antibody, so long as that fragment includes the site responsible for binding to activated platelets. Without wishing to be limited by theory it is thought that the compact dimensions of a single-chain antibody is of particular advantage in this application. It is proposed that the antibody is capable of penetrating beyond the surface of a thrombus into areas where a greater number of activated platelets are present. This allows for more effective detection of the bound antibody, and therefore higher sensitivity imaging.

The method may be used to diagnose and identify thrombi (e.g. deep vein thrombosis), thrombotic emboli (e.g. pulmonary embolism) and deposition of activated platelets (e.g. at the site of unstable atherosclerotic plaques). Early detection will be highly advantageous allowing the administration of clot dissolving agents and/or anticoagulant therapy and/or interventional procedures.

An additional molecule that may be utilised in the methods of this aspect of the invention is fibrin, a latter stage component of a clot. Fibrin is involved in newly forming clots after cleavage by thrombin from fibrinogen. Accordingly, there is provided a method of detecting blood coagulation disorders including the steps of administering a contrast agent to a mammal wherein the contrast agent includes a targeting molecule capable of binding fibrin;

allowing the MRI contrast agent to bind to the cellular target; and imaging the mammal to generate a MR image.

Preferably the targeting molecule is a single chain monoclonal antibody which selectively binds to the amino-terminus of the fibrin beta-chain.

It will be understood that the invention disclosed and defined in this specification extends to all alternative combinations of two or more of the individual features mentioned or evident from the text or drawings. All of these different combinations constitute various alternative aspects of the invention.

The present invention will now be more fully described with reference to the accompanying examples. It should be understood, however, that the description following is illustrative only and should not be taken in any way as a restriction on the generality of the invention described above.

Examples

The invention will now be described with reference to the following non-limiting illustrative examples and figures.

A system of nomenclature has been developed for the purposes of identifying the individual compounds described in this patent. This nomenclature is used to simplify the description of the compounds and is used in place of what would be a complex IUPAC name, the use of which may be prone to error and difficult to interpret.

The dendrimer nomenclature makes use of the following abbreviations:

| Abbreviation | Name | Structure[1] |
| --- | --- | --- |
| NEOEOEN | | |
| Su(NPN)$_2$ | | |
| Lys | Lysine | |
| NH2•TFA | Represents the surface amine groups of the deprotected molecule as the TFA salt | |
| Boc | t-butyloxycarbonyl | |
| Fmoc | flourenylmethoxycarbonyl | |
| CBz | Benzyloxycarbonyl | |

-continued

| Abbreviation | Name | Structure[1] |
|---|---|---|
| MAL | Maleimide | |
| MAL—(CH$_2$)$_2$—CO— | 3-maleimidopropanoic acid | |
| [CBz]NEOEOEN | Benzyloxycarbonylamino-3,6-oxa-8-aminooctane | |
| DBL—OPNP | p-nitrophenyl active ester of di-Boc Lysine | |
| HO—Su(NPN)$_2$ [Boc]$_2$ | | |
| PNPO—Su(NPN)$_2$ [Boc]$_2$ | | |
| MeOGly•HCl | | |

| Abbreviation | Name | Structure[1] |
|---|---|---|
| PNPO-α-Boc-ε-CBz-Lys | | |

[1]Asterisk indicates amine group bonded as amide to carboxyl group of lysine branching unit or capping moiety. Hash indicates carboxyl group bonded as amide to amine of core or lysine branching unit.

The dendrimer nomenclature makes use of the following form:

Core [Last Complete Layer: Repeating Unit]$_n$[Capping agent]$_m$[Incomplete Outer Layer: Building Unit]$_p$[Capping agent]$_q$ Where:
Core is the tri-amino moiety to which the first layer of lysine repeating units is added,
n is the number of lysine repeating units on the outermost complete layer of the dendrimer, p is the number of lysine repeating units on the incomplete outer layer of the dendrimer,
m is the number of Capping agents, for example mannose moieties or terminal amine protecting groups, on the outermost complete layer of building units; q is the number of Capping agents on the incomplete outer layer of building units,
Optionally, a Capping group and/or building unit may be appended to the core;
these are then denoted using a prefix of [Capping agent]$_v$[repeating unit]$_s$ following the same principles as above.

Exemplary macromolecules contemplated herein may be conveniently represented according to the following formula:

[First Functional moiety]Core[Building Unit]$_m$[Second Functional Moiety]$_p$ [Third functional moiety]$_q$ wherein:
the core and building units are as described herein and the functional moieties are selected front targeting molecules and signalling entities;
m represents the sum of the building units (including the surface and subsurface layers) or the macromolecule. By way of example, where each layer comprises building units having 2 amino groups, m is an integer from 2 to 32, for example, 2, 4, 8, 16 or 32;
p represents the number of second functional moieties attached to the amino nitrogen atoms at the surface (uttermost) layer of building units. By way of example, where each layer comprises building units having 2 amino groups, p is an integer from 1 to 64, for example, 2, 4, 8, 16, 32 or 64;
q represents the number of third functional moieties attached to amino nitrogen atoms at the surface (outermost layer of building units. By way of example, where each layer comprises building units having 2 amino groups, q may be an integer from 0 to 63 such that pa do q is not greater than 64.

The nomenclature functions to completely describe the size of a dendrimer through provision of the core and the outer layer since only lysine repeating units are used in the construction of these dendrimer structures and the valency of the core is known, and further since all of the terminal nitrogen groups of each dendrimer layer are completely reacted with lysine during the addition of a new lysine layer.

Further abbreviations are as follows:

| Abbreviation | Full Name |
|---|---|
| PyBop | Benzotriazole-1-yl-oxy-tris-pyrrolidino-phosphonium hexafluorophosphate |
| DIPEA | N,N-Diisopropylethylamine |
| DCC | 1,3-Dicyclohexylcarbodiimide |
| HOBt | 1-Hydroxybenzotriazole hydrate |
| NaH | Sodium Hydride |
| BnBr | Benzyl bromide |
| TBDMSCl | t-butyldimethylsilyl chloride |
| EtAlCl$_2$ | Ethyl Aluminium dichloride |
| TFA | Trifluoroacetic acid |
| DCM | Dichloromethane |
| EtOAc | Ethyl acetate |
| MeOH | Methanol |
| MeCN | Acetonitrile |
| DMF | Dimethylformamide |
| DMSO | Dimethylsulfoxide |
| PBS | Phosphate buffered saline |
| TLC | Thin Layer Chromatography |
| HPLC | High Performance Liquid Chromatography |
| MS | Mass Spectrometry |
| DPTA | Diethylene triamine pentaacetic acid |
| DOTA | 1,4,7,10-tetraazacyclododecane-1,4,7,10-tetraacetic acid |

HPLC and MS equipment details:
HPLC—Waters 2795 with 2996 Diode Array Detector (DAD)
MS—Waters ZQ4000 with ESI probe, inlet flow split to give around 50 μL/min to the MS.

Mass Spectra data was acquired in positive or negative electrospray ionisation mode as indicated. The raw data was deconvoluted using a Maximum Entropy algorithm (MaxEat) as implemented in MassLynx software v4.0, supplied by Waters Corporation. The data reported in the experimental details corresponds to the observed value after deconvolution to a theoretical zero charge state.

Example 1

[CBz]NEOEOEN[Su(NPN)$_2$][Boc]$_2$ i. Benzyloxycarbonylamino-3,6-oxa-8-aminooctane: [CBz]NEOEOEN To a solution of 2,2'-(ethylenedioxy)diethylamine (4.45 g, 30 mmol) and TEA (0.7 mL, 50 mmol) in MeCN (50 mL), was added dropwise over 20 min a solution of N-(benzyloxycarbonyloxy)succinimide (1.2 g, 5.0 mmol) in MeCN (10 mL). Once the addition was complete the solution was stirred at room temperature overnight. Acetonitrile was removed in vacuo and the resulting colourless residue redissolved in water (50 mL). The aqueous solution was washed with DCM (3×25 mL) and the combined organic extracts reduced in vacua. The residue was dissolved in 2M HCl (25 mL) and washed with diethyl ether (3×25 mL). The aqueous layer was then neutralized to pH 7 with NaOH and evaporated to dryness in vacuo. The resulting residue was added to EtOAc (25 mL), filtered and dried over $Na_2SO_4$. Removal of solvent in vacua provided a colourless oil (840 mg, 2.9 mmol, 60%). ESI MS (+ve) 283 [M+H]$^+$; calc. m/z for $C_{14}H_{22}N_2O_4$ [M+H]$^+$: 283.34.

ii. tert-Butyl 2-({2-[(tert-butoxycarbonyl)amino]propyl}amino)propylcarbamate

A solution of dipropylenetriamine (171 g, 1.32 mol) in THF (200 mL) was added dropwise over 1 h, to a solution of tert-butyl-1H-imidazole-1-carboxylate (444 g, 2.64 mol) in THF (1.2 L) at room temperature. The resulting solution was refluxed for 4 h and then stirred at room temperature overnight. The THF was removed in vacuo and the residue dissolved in DCM (2 L). The DCM solution Was first washed with NaOH (2M, 2×1 L) and then citric acid 10% w/v (2×1 L). Both the DCM and NaOH solutions were discarded. The aqueous citric acid solution was basified with NaOH (4 M, until pH 14), extracted with DCM (3×600 mL) and the combined DCM extracts concentrated in vacuo to afford a clear oil, which solidified on cooling to yield a white solid (346 g, 80%).

iii. HO—Su(NPN)$_2$[Boc]$_2$

A 3 L vessel fitted with an overhead stirrer was charged with tert-Butyl 2-({2-[(tert-butoxycarbonyl)amino]propyl}amino)propylcarbamate (208.5 g, 0.63 mol) and toluene (900 mL). Succinic anhydride (63 g, 0.63 mol) was added in one portion and the resulting solution heated at 60° C. overnight. The mixture was cooled to room temperature, diethyl ether was added (1×200 mL) and the solid filtered. The solid was washed with diethyl ether (2×200 mL) and dried to yield a white solid (230 g, 91%).

iv. [CBz]NEOEOEN[Su(NPN)$_2$][Boc]$_2$

To a solution of [CBz]NEOEOEN (Example 1i) (440 mg, 1.6 mmol) in DMF (4 mL), was added TEA (0.22 mL, 1.6 mmol) and PNPO—Su(NPN)$_2$-Boc$_2$ (950 mg, 1.8 mmol). The solution was stirred at room temperature overnight. Solvent was removed in vacuo and the residue dissolved in EtOAc (250 mL). This solution was washed with brine (125 mL), 1M $Na_2CO_3$ (3×50 mL), water (125 mL), 1M KHSO$_4$ and a second wash of brine (125 mL) before drying over $Na_2SO_4$. The solution was concentrated in vacuo and purified by silica gel chromatography (MeOH/DCM gradient) to provide a clear viscous oil (165 mg, 0.23 mmol, 15%). ESI MS (+ve) 496 [M+H]$^+$; calc. m/z for $C_{24}H_{41}N_5O_6$ [M+H]$^+$: 496.61.

Example 2

[CBz]NEOEOEN[Su(NPN)$_2$][Lys]$_2$[Boc]$_4$

[CBz]NEOEOEN[Su(NPN)$_2$][Boc]$_2$ (Example 1iv) (13.89 g, 20.0 mmol) was dissolved in acetic acid (50 mL) and the stiffed solution cooled in an ice bath. Ice cooled TEA (50 mL, 0.73 mol) was added at a rate that maintained the temperature of the solution at or below 5° C. The ice bath was removed and the solution stirred at room temperature for 5 h. It was then cooled and ice-cooled water (100 mL) was added at a rate that kept the mixture below 5° C. The volatiles were evaporated in vacuo and water (100 mL) was added to the oily residue. The solution was then concentrated in vacuo and the process was repeated with more water (2×100 mL). The oil was dissolved in water (50 mL), the solution filtered and freeze dried to give [CBz]NEOEOEN[Su(NPN)$_2$][NH$_2$.TFA]$_2$ (17.1 g) as a colourless glassy solid. $^1$H-NMR (300 MHz, CD$_3$OD) δ (ppm) 1.90 (apparent quintet, J=6.6 Hz, 2H); 1.99 (m, 2H); 2.57 (m, 2H); 2.65 (m, 2H); 2.89 (t, J=6.6 Hz, 2H); 3.00 (t, J=7.5 Hz, 2H); 3.30-3.38 (complex, 6H); 3.42-3.58 (complex, 6H); 3.61 (s, 4H); 5.08 (s, 2H); 7.25-7.40 (complex, 5H); HPLC (Hydrophilic/TFA) Rt=8.0 min; ESI MS (+ve) 496.2 [M+H]$^+$; calc. m/z for $C_{24}H_{42}N_5O_6^+$ [M+H]$^+$: 496.3.

A solution of DBL-OPNP (12.8 g, 17.7 mmol) in DMF (80 mL) was added to a solution of [CBz]NEOEOEN[Su(NPN)$_2$][NH$_2$.TFA]$_2$ (19.5 g, 35.4 mmol) and TEA (17.9 g, 0.177 mol) in DMF (80 mL) at room temperature. After stirring for 16 h, a solution of glycine (1.50 g, 29.0 mmol) in water (50 mL) was added and stirring continued for 16 h. Volatiles were removed in vacuo, the residue dissolved in EtOAc (200 mL) and the solution washed sequentially with 5% w/v $Na_2CO_3$ (10×50 mL), brine (50 mL), 1M HCl (2×50 mL) and again with brine (50 mL). The EtOAc solution was dried (Na$_2$SO$_4$), filtered and the solvent removed in vacua to give the product as a colourless oil (20.74 g). $^1$H-NMR (300 MHz, CD$_3$OD) δ (ppm) 1.15-1.95 (complex, 16H); 1.43 (s, 18H); 1.44 (s, 18H); 2.51 (m, 2H); 2.64 (in, 2H); 3.02 (t, J 6.6 Hz, 4H); 3.17 (m, 2H); 3.25-3.45 (complex, 8H); 3.48-3.58 (complex, 4H); 3.61 (s, 4H); 5.08 (s, 2H); 7.25-7.40 (complex, 5H). HPLC (Hydrophobic/TPA) Rt=8.6 min; ESI MS (+ve) 1153.0 [M+H]$^+$; calc. m/z for $C_{56}H_{98}N_9O_{16}^+$ [M+H]$^+$: 1152.7.

Example 3

[CBz]NEOEOEN[Su(NPN)$_2$][Lys]$_4$[Boc]$_8$

[CBz]NEOEOEN[Su(NPN)$_2$][Lys]$_2$[Boc]$_4$ (20.74 g, 18.0 mmol) was dissolved in acetic acid (50 mL) and the stirred solution cooled in an ice bath. Ice cooled TFA (50 mL, 0.73 mol) was added at a rate that maintained the temperature of the solution at or below 5° C. The ice bath was removed and the solution stirred at room temperature for 5 h. The solution was then cooled to 5° C. and added to ice-cold water (100 mL) at a rate that kept the mixture below 5° C. Volatiles were evaporated in vacua and water (100 mL) was added to the residual oil. The resultant solution was then concentrated in vacua and the process was repeated with more water (2×100 mL). The oil was dissolved in water (50 mL), the solution filtered and freeze dried to give a foamy solid. Analysis of this material by $^1$H-NMR and HPLC/ESI MS showed that removal of the Boc groups was incomplete. The partially deprotected material was treated with acetic acid (50 mL) and TFA (50 mL) and reprocessed as above to give [CBz]NEOEOEN[Su(NPN)$_2$][Lys]$_2$[NH$_2$.TFA]$_4$ (25.1 g) as a pale yellow glassy solid, $^1$H-NMR (300 MHz, D$_2$O) δ (ppm) 1.44 (m, 4H); 1.70 (m, 6H); 1.86 (m, 6H); 2.50 (m, 2H); 2.64 (m, 2H); 2.99 (t, J 7.2 Hz, 2H); 3.12-3.47 (complex, 12H); 3.52-3.63 (complex, 12H); 3.95 (m, 2H); 5.12 (s, 2H); 7.32-7.50

(complex, 5H); HPLC (Hydrophilic/TFA) Rt=10.4 min; ESI MS (+ve) 752.4 [M+H]$^+$; calc. m/z for $C_{36}H_{66}N_9O_8^+$ [M+H]$^+$: 752.5.

A solution of DBL-OPNP (16.8 g, 13.9 mmol) in DMF (100 mL) was added to a solution of [CBz]NEOEOEN[Su (NPN)$_2$][Lys]$_2$[NH$_2$.TFA]$_4$ (33.98 g, 61.3 mmol) and TEA (13.5 g, 0.134 mol) in DMF (100 mL) at room temperature. After stirring for 11 h, a 1M aqueous solution of glycine (10 mL) was added; the same quantity of glycine solution was added again after 1 h and again 1.5 h later. Stirring was continued for a further 2 h and the volatiles were then evaporated in vacuo. The residue was dissolved in EtOAc (200 mL) and the solution washed sequentially with 0.5 M HCl (2×50 mL), 10% w/v Na$_2$CO$_3$ (6×50 mL) and brine (50 mL). The EtOAc solution was dried (Na$_2$SO$_4$), filtered and the solvent removed in vacuo to give the desired product as a colourless oil (26.26 g, 91%). $^1$H-NMR (300 MHz, d$_6$-DMSO) δ (ppm) 1.00-1.75 (complex, 112H); 2.32 (m, 2H); 2.47 (m, 2H); 2.75-3.50 (complex, 32H); 3.75-3.90 (complex, 4H); 4.10-4.25 (complex, 2H); 5.01 (s, 2H); 6.38 (br. m, 1H); 6.60-6.95 (complex, 8H); 7.25 (m, 1H); 7.28-7.39 (complex, 5H); 7.60-8.05 (complex, 7H). HPLC (Hydrophobic/TFA) Rt=15.2 min; ESI MS (+ve) 1033.8 [M+2H]$^{2+}$/2; calc. m/z for $C_{100}H_{179}N_{17}O_{28}^{2+}$ [M+2H]$^{2+}$/2: 1033.7.

Example 4

[CBz]NEOEOEN[Su(NPN)$_2$][Lys]$_8$[Boc]$_{16}$

[CBz]NEOEOEN[Su(NPN)$_2$][Lys]$_4$[Boc]$_8$ (24.52 g, 11.9 mmol) was dissolved in acetic acid (108 mL) and the stirred solution cooled in an ice bath until the acetic acid began to freeze. TFA (108 mL, 1.40 mol) was then added at a rate that maintained the temperature of the solution at or below 10° C. The ice bath was then removed and the solution stirred at room temperature for 15 h. The acetic acid and TFA were evaporated in vacuo and water (100 mL) was added to the residual oil. The solution was then concentrated in vacuo and the process was repeated with more water (3×100 mL). The resultant oil was dissolved in water (100 the solution filtered and then freeze dried to give [CBz]NEOEOEN[Su(NPN)$_2$] [Lys]$_4$[NH$_2$.TFA]$_8$ (29.2 g) as a colourless glassy solid. $^1$H-NMR (300 MHz, D$_2$O) δ (ppm) 1.25-2.05 (complex, 40H); 2.53 (m, 2H); 2.65 (m, 2H); 2.95-3.10 complex, 8H); 3.10-3.45 (complex, 16H); 3.55-3.75 (complex, 8H); 3.95 (t, J 6.6 Hz, 2H); 4.06 (t, J 6.6 Hz, 2H); 4.20-4.30 (complex, 2H); 5.15 (s, 2H); 7.35-7.55 (complex, 5H); HPLC (Hydrophilic/Formate) Rt=8.4 min; ESI MS (+ve) 1265.1 [M+H]$^+$, 633.0 [M+2H]$^{2+}$/2; calc. m/z for $C_{60}H_{114}N_{17}O_{12}^+$ [M+H]$^+$: 1264.9, calc. m/z for $C_{60}H_{115}N_{17}O_{12}^{2+}$ [M+2H]$^{2+}$: 633.0.

A solution of DBL-OPNP (48.2 g, 87.2 mmol) in DMF (120 mL) was added to a solution of [CBz]NEOEOEN[Su (NPN)$_2$][Lys]$_4$[NH$_2$.TFA]$_8$ (25.83 g, 11.87 mmol) and Et$_3$N (23.1 g, 0.228 mol) in DMP (150 mL) at room temperature. After stirring for 19 h, a solution of glycine (3.27 g, 43.6 mmol) in water (80 mL) was added. Stirring continued for 2 h and then the volatiles were evaporated in vacuo. The residue was dissolved in EtOAc (200 mL) and the solution washed sequentially with 5% w/v Na$_2$CO$_3$ (1×100 mL; 4×50 mL), 1M HCl (2×50 mL) and again with brine (50 mL). The EtOAc solution was dried (Na$_2$SO$_4$), hot filtered and the solvent removed in vacuo to give the desired product as a yellow glassy solid (27.12 g, 59%). Some of the product precipitated in the fluted filter paper; dissolution of this material in methanol, filtration and removal of methanol in vacuo gave additional product (9.02 g, 20%) as a yellow foam. Analysis of both portions of the product gave identical sets of $^1$H-NMR and ESI MS data. $^1$H-NMR (300 MHz, CD$_3$OD) δ (ppm) 1.00-1.75 (complex, 232H); 2.51 (m, 2H); 2.65 (m, 21-1); 2.75-3.50 (complex, 40H); 3.50-3.65 (complex, 8H); 3.90-4.50 (complex, 14H); 5.08 (s, 2H); 7.25-7.40 (complex, 5H). HPLC (Hydrophobic/TFA) Rt=19.7 min; ESI MS (+ve) 1947.3 [M+2H]$^{2+}$/2, 12983 [M+3H]$^{3+}$/3; calc. m/z for $C_{188}H_{339}N_{33}O_{52}^{2+}$ [M+2H]$^{2+}$/2: 1946.8, calc. m/z for $C_{188}H_{340}N_{33}O_{52}^{3+}$ [M+3H]$^{3+}$/3; 1298.2.

Example 5

[CBz]NEOEOEN[Su(NPN)$_2$][Lys]$_{16}$[Boc]$_{32}$

[CBz]NEOEOEN[Su(NPN)$_2$][Lys]$_8$[Boc]$_{16}$ (25.75 g, 6.62 mmol) was dissol acid (122 mL) and the stirred solution cooled in an ice bath until the acetic acid began to freeze. The ice bath was removed and TFA was carefully added until the acetic acid just melted. The stirred solution was once again placed in the ice bath and the remainder of the TFA (total amount of TFA used was 108 mL, 1.40 mol) was then added at a rate that maintained the temperature of the solution at or below 10° C. The ice bath was removed and the solution stirred at room temperature for 17 h. The solution was cooled on ice and then added to ice cold water (400 mL) while making sure that the temperature of the resultant solution remained below 10° C. The volatile components were evaporated in vacua and water (250 mL) was added to the oily residue. The solution was then concentrated in vacuo and the process was repeated with more water (2×250 mL). The final oil was dissolved in water (200 mL), the solution filtered and freeze dried to give [CBz]NEOEOEN[Su(NPN)$_2$][Lys]$_8$ [NH$_2$.TFA]$_{16}$ (27.6 g) as a colourless glassy solid. $^1$H-NMR (300 MHz, D$_2$O) δ (ppm) 1.25-1.65 (complex, 40H); 1.65-2.05 (complex, 48H); 2.50 (m, 2H); 2.62 (m, 2H); 2.95-3.05 (complex, 16H); 3.05-3.45 (complex, 24H); 3.55-3.70 (complex, 8H); 3.94 (t, J 6.6 Hz, 4H); 4.05 (t, J 6.6 Hz, 4H); 4.15-4.30 (complex, 4H); 4.30-4.40 (complex, 2H); 5.13 (s, 2H); 7.35-7.50 (complex, 5H); HPLC (Hydrophilic/TFA) Rt=8.9 min; ESI MS (+ve) 763.9 [M+3H]$^{3+}$/3, 573.4 [M+4H]$^{4+}$/4; calc. m/z for $C_{108}H_{212}N_{33}O_{20}^{3+}$ [M+3H]$^{3+}$: 764.2, calc, m/z for $C_{108}H_{213}N_{33}O_{20}^{4+}$ [M+4H]$^{4+}$; 573.4.

DBL-OPNP (27.66 g, 59.2 mmol) was added in ca. 2-3 g portions to a solution of [CBz]NEOEOEN[Su(NPN)$_2$] [Lys]$_8$[NH$_2$.TFA]$_{16}$ (13.83 g, 3.36 mmol) and Et$_3$N (13.1 g, 0.129 mol) in DMP (150 mL) at room temperature. After stirring for 17 h, a solution of glycine (2.22 g, 29.6 mmol) in water (50 mL) was added. Stirring was continued for 3 h and the solution was then added to rapidly stirred water (400 mL). The supernatant liquid was decanted from the resultant precipitated gum. The gummy material was dissolved in DMF (100 mL) and the solution added slowly to a well stirred mixture of flaked ice (500 g) and water (500 mL). The precipitated white solid was collected by filtration, resuspended in 5% w/v Na$_2$CO$_3$, sonicated and filtered again. The solid was washed thoroughly with water (4×100 mL) and dried to give the desired product (22.10 g, 87%) as a beige powder. $^1$H-NMR (300 MHz, CD$_3$OD) δ (ppm) 1.10-1.95 (complex, 472H); 2.52 (m, 2H); 2.65 (m, 2H); 2.95-3.10 (complex, 30H); 3.10-3.30 (complex, 30H); 3.30-3.45 (complex, 12H); 3.45-3.65 (complex, 8H); 3.80-4.15 (complex, 16H); 4.20-4.45 (complex, 14H); 5.09 (s, 2H); 7.25-7.40 (complex, 5H). Due to insolubility in the HPLC mobile phase, HPLC and ESI MS data for this product could not be obtained. Instead, the Boc groups were removed and these data were obtained from the derived poly trifluoroacetate salt:

[Cbz]NEOEOEN[Su(NPN)$_2$][Lys]$_{16}$[Boc]$_{32}$ (389 mg, 51.6 μmol) was dissolved in acetic acid (1.9 mL) and the stirred solution cooled to 0° C. until the acetic acid began to freeze. TFA (1.9 mL, 24.8 mmol) was carefully added until the acetic acid just melted. The solution was stirred at room temperature for 21 h. The volatiles were removed in vacuo and water (5 mL) was added to the oily residue. The solution was then concentrated in vacuo and the process was repeated with more water (2×5 mL). The final oil was dissolved in water (5 mL), filtered and freeze dried to give [Cbz] NEOEOEN[Su(NPN)$_2$][Lys]$_{16}$[TFA]$_{32}$ (397 mg, 96%) as an amorphous white solid. $^1$H-nmr (300 MHz, D$_2$O) δ (ppm) 1.20-1.65 (complex, 92H); 1.65-1.85 (complex, 62H); 1.85-2.05 (complex, 30H); 2.51 (m, 2H); 2.61 (m, 2H); 2.95-3.10 (complex, 34H); 3.10-3.45 (complex, 38H); 3.55-3.70 (complex, 8H); 3.94 (t, J 6.6 Hz, 8H); 4.05 (t, J 6.6 Hz, 8H); 4.15-4.28 (complex, 8H); 428-4.39 (complex, 6H); 5.00 (s, 2H); 7.32-7.49 (complex, 5H); HPLC (Hydrophilic/TPA) Rt=8.8 min; ESI MS (+ve) 1447.8 [M+3H]$^{3+}$/3, 1086.1 [M+4H]$^{4+}$/4; calc. m/z for $C_{204}H_{404}N_{65}O_{36}{}^{3+}$ [M+3H]$^{3+}$: 1447.1, calc. m/z for $C_{204}H_{405}N_{65}O_{36}{}^{4+}$ [M+4H]$^{4+}$: 1085.6.

Example 6

[MAL-(CH$_2$)$_2$CO]NEOEOEN[Su(NPN)$_2$][Lys]$_{16}$[Gd-GlyMeDOTA]$_{32}$

The preparation of the title compound is illustrated with reference to FIG. 3. Gd-GlyMeDOTA NHS ester was prepared as described in U.S. Pat. No. 6,045,776.

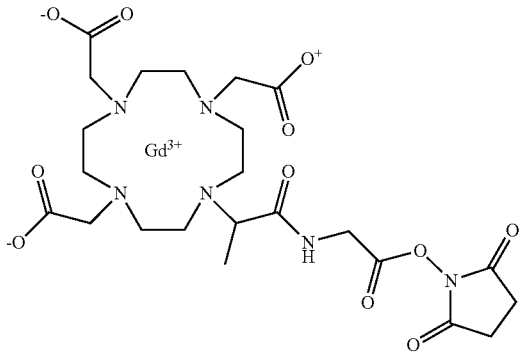

The reaction scheme is as follows:
1 (R$_1$=Boc, R$_2$=CBz) [CBz]NEOEOEN[Su(NPN)$_2$][Lys]$_{16}$[Boc]$_{32}$ could be treated with TFA/acetic acid to provide 2a (R$_1$=H, R$_2$=CBz) [CBz]NEOEOEN[Su(NPN)$_2$][Lys]$_{16}$[NH$_2$.TFA]$_{32}$; upon reaction of 2a with the NHS ester of Gd-GlyMeDOTA in DMSO; 2c (R$_1$=Gd-GlyMeDOTA, R$_2$=CBz) [CBz]NEOEOEN[Su(NPN)$_2$][Lys]$_{16}$[Gd-GlyMeDOTA]$_{32}$ could be provided; the CBz group could be removed (Pd/C, ammonium formate, DMF/H$_2$O), to provide 2d (R$_1$=Gd-GlyMeDOTA, R$_2$=H) [NH$_2$]EOEOEN[Su(NPN)$_2$][Lys]$_{16}$[Gd-GlyMeDOTA]$_{32}$, which could then be reacted with 3-maleimidopropanoic acid (NHS ester) and DIPEA in DMSO, to provide 2e (R$_1$=Gd-GlyMeDOTA, R$_2$=MAL-(CH$_2$)$_2$CO) [MAL-(CH$_2$)$_2$CO]NEOEOEN[Su(NPN)$_2$][Lys]$_{16}$[Gd-GlyMeDOTA]$_{32}$.

Example 7

MAL-(CH$_2$)$_2$CONH-PEG$_{1100}$-CO-NEOEOEN[Su(NPN)$_2$][Lys]$_8$[Su-p-Bn-DTPA]$_{16}$ i. HO-Su-p-Bn-DTPA-O$^t$Etu

To p-NH$_2$—Bn-DTPA-O$^t$Bu (100 mg, 0.128 mmol) in DMF (5 mL) was added TEA (50 µL, 0.35 mmol) and succinic anhydride (25 mg, 0.25 mmol). The mixture was stirred at room temperature for 16 h. The solvents were evaporated in vacuo to give a crude oil which was purified by silica gel chromatography (eluents: 15-20% MeOH/DCM) to provide HO-Su-p-Bn-DTPA-O$^t$Bu (110 mg, 97%), HPLC/MS (Hydrophobic/TFA) Rt=5.76 min; ESI MS (+ve) m/z=880 [M+1H]; calc. m/z for $C_{45}H_{74}N_4O_{13}$; 879.1 g/mol.

ii. [Cbz]NEOEOEN[Su(NPN)$_2$]Lys$_8$[Su-p-Bn-DTPA-O$^t$Bu]$_{16}$

To a stirred mixture of [Cbz]NEOEOEN[Su(NPN)$_2$]Lys$_8$[NH$_2$.TFA]$_{16}$ (135 mg, 0.033 mmol) and HO-Su-p-Bn-DTPA-O$^t$Bu (600 mg, 0.68 mmol) in DMF (20 mL) at 0° C. was added DIPEA (289 µL, 1.91 mmol) and PyBop (630 mg, 1.21 mmol). The mixture was allowed to warm to room temperature and stirred for 16 h. The solvents were evaporated in vacuo to give a crude oil, which was purified by Sephadex (eluent, MeOH) to provide [Cbz]NEOEOEN[Su(NPN)$_2$]Lys$_8$[Su-p-Bn-DTPA-O$^t$Bu]$_{16}$ (350 mg, 66%) as a white foam. HPLC/MS (Hydrophobic/TFA) Rt=8.15 min; ESI MS (+ve) m/z=16070; calc. m/z for $C_{828}H_{1360}N_{97}O_{212}$: 16066.1 g/mol.

iii. [NH$_2$]EOEOEN[Su(NPN)$_2$]Lys$_8$[Su-p-Bn-DTPA-O$^t$Bu]$_{16}$

To a solution of [Cbz]NEOEOEN[Su(NPN)$_2$]Lys$_8$[Su-p-Bn-DTPA-O$^t$Bu]$_{16}$ (130 mg, 8.1 µmol) in 9:1 DMF/H$_2$O (10 mL) was added HCOONH$_4$ (150 mg, 2.45 mmol) and 10% Pd—C (130 mg, 0.13 mmol). The suspension was stirred at room temperature for 16 h. The suspension was then filtered through a 0.45 micron filter and the filtrate reduced in vacuo to provide [NH$_2$]EOEOEN[Su(NPN)$_2$]Lys$_8$[Su-p-Bn-DTPA-O$^t$Bu]$_{16}$ as a clear viscous oil. (120 mg, 93%). HPLC/MS (Hydrophobic/TPA) Rt=8.06 min; ESI MS (+ve) m/z=15940, calc. m/z for $C_{820}H_{1354}N_{97}O_{210}$: 15931.9 g/mol.

iv. MAL-(CH$_2$)$_2$CONH-PEG$_{1100}$-CO-NEOEOEN[Su(NPN)$_2$][Lys]$_8$[Su-p-Bn-DTPA-O$^t$Bu]$_{16}$

To a solution of [NH]EOEOEN[Su(NPN)$_2$]Lys$_8$[Su-p-Bn-DTPA-O$^t$Bu]$_{16}$ (30 mg, 1.8 µmol) in DCM (5 mL) was added TEA (150 µL, 1.04 mmol) and then MAL-PEG$_{1100}$-NHS (11 mg, 7.9 µmol). The solution was stirred at room temperature for 16 h. The reaction solution was concentrated in vacuo to give an oil which was purified by HPLC (eluents; CH$_3$CN/H$_2$O/0.1% TFA) to provide MAL-(CH$_2$)$_2$CONH-PEO$_{1100}$-CO-NEOEOEN[Su(NPN)$_2$][Lys]$_8$[Su-p-Bn-DTPA-O$^t$Bu]$_{16}$ as a foam (11 mg, 32%). HPLC/MS (Hydrophobic/TFA) Rt=8.04 min; ESI MS (+ve) m/z=17220; calc. m/z for $C_{878}H_{1460}N_{99}O_{233}$: 17211.4 g/mol.

v. MAL-(CH$_2$)$_2$CONH-PEG$_{1100}$-CO-NEOEOEN[Su(NPN)$_2$][Lys]$_8$[Su-p-Bn-DTPA]$_{16}$

To MAL-(CH$_2$)$_2$CONH-PEG$_{1100}$-CO-NEOEOEN[Su(NPN)$_2$][Lys]$_8$[Su-p-Bn-DTPA-O$^t$Bu]$_{16}$ (3.5 mg, 0.2 µmol) was added 20% TFA/DCM (3 mL). The solution was stirred at room temperature for 2 h. The reaction solution was concentrated in vacuo to provide MAL-(CH$_2$)$_2$CONH-PEG$_{1100}$-CO-NEOEOEN[Su(NPN)$_2$][Lys]$_8$[Su-p-Bn-DTPA]$_{16}$ as a foam (3.5 mg). HPLC/MS (Hydrophilic/TFA) Rt=9.40 min (broad peak); ESI MS (+ve) m/z: no mass spectrum was obtained for this compound ($C_{558}H_{820}N_{99}O_{238}$).

Example 8

N-Fluorescein cadaverine

Fluorescein N-hydroxysuccinimidyl ester (30 mg, 0.063 mmol) in DMF (1 mL) was added to a stirred solution of 1.5 diaminopentane dihydrochloride (66 mg, 0.32 mmol) in pH 8.4 buffer solution (0.1 M $Na_2HPO_4$/0.1 M HCl, 2 mL) under inert atmosphere at room temperature. The solution was stirred for 12 h then the solvents were evaporated in vacua. The crude mixture was purified by HPLC to give N-Fluorescein cadaverine as a yellow oil (20 mg, 68%). HPLC/MS (Hydrophilic/TFA) Rt=6.67 min; ESI MS (+ve) m/z=461 [M+1H]; calc. m/z for $C_{24}H_{26}N_2O_6$: 460.5 g/mol.

Example 9

[TFA.$NH_2(CH_2)_5$NHSu]NEOEOEN[Su(NPN)$_2$]Lys$_8$[Su-p-Bn-DTPA]$_{16}$ i. BocNH$(CH_2)_5NH_2$ (N-Boc-cadaverine)

A solution of 2-(Boc-oxyimino)-2-phenylacetonitrile (226 mg, 0.92 mmol) in 1,4-dioxane (30 mL) was added via syringe pump (rate=8 mL/hr) to a stirred solution of 1,5 diaminopentane dihydrochloride (1 g, 5.52 mmol) and TEA (1 ml, 7.12 mmol) in 1:1 1,4-dioxane:water (40 mL) under inert atmosphere at room temperature. The reaction was stirred for 12 h and DCM (20 mL) was added to the reaction mixture. The organic phase was extracted and concentrated in vacuo. The yellow residue was dissolved in diethyl ether (15 mL) and 5% HCl solution added. The acidic solution was washed with diethyl ether and then the pH of the aqueous layer adjusted to pH 14 with 2.5M NaOH solution. Ethyl acetate (20 mL) was added and the organic layer was washed with brine (2×50 mL), and dried ($MgSO_4$). The solvents were evaporated in vacua to yield N-Boc-cadaverine as a yellow oil (100 mg, 55%). HPLC/MS (Hydrophilic/TFA) Rt=6.17 min; ESI MS (+ve) m/z=203 [M+1H]; calc. m/z for $C_{10}H_{22}N_2O_2$: 202.3 g/mol, ii [HO-Su]NEOEOEN[Su(NPN)$_2$]Lys$_8$[Su-p-Bn-DTPA-O$^t$Bu]$_{16}$

To a stirred solution of [$NH_2$]EOEOEN[Su(NPN)$_2$]Lys$_8$[Su-p-Bn-DTPA-O$^t$Bu]$_{16}$ (20 mg, 1.3 µmol) in DMF (1 mL) was added TEA (150 µL, 1.04 mmol) and succinic anhydride (2 mg, 0.02 mmol), the mixture was stirred for 16 h. The reaction solution was then diluted with DCM (2 mL), and to the solution was added N-(2-aminoethyl)aminomethyl polystyrene (20 mg, 0.06 mmol) and the mixture stirred at room temperature for 2 h. The reaction mixture was then filtered through a 0.45 micron filter and the filtrate reduced in vacuo to provide [HO-Su]NEOEOEN[Su(NPN)$_2$]Lys$_8$(Su-p-Bn-DTPA-O$^t$Bu]$_{16}$ as a clear viscous oil. (20 mg). HPLC/MS (Hydrophobic/TFA) Rt=8.11 min; ESI MS (+ve) m/z=16030; calc. m/z for $C_{824}H_{1358}N_{97}O_{213}$: 16032.0 g/mol.

iii. [BocNH$(CH_2)_5$NHSu]NEOEOEN[Su(NPN)$_2$] Lys$_8$[Su-p-Bn-DTPA-O$^t$Bu]$_{16}$ To a stirred solution of [HO-Su]NEOEOEN[Su(NPN)$_2$] Lys$_8$[Su-p-Bn-DTPA-O$^t$Bu]$_{16}$ (20 mg, 1.3 µmol) and N-Boc-cadaverine (2 mg, 9.9 µmol) in DMF (1 mL) at 0° C. was added DIPEA (289 µL, 139 µmol) and PyBop (10 mg, 19 µmol). The mixture was allowed to warm to room temperature and stirred for 40 h. The solvents were evaporated to give a residue, which was purified by HPLC (eluents $CH_3CN$/$H_2O$/0.1% TFA) to provide [BocNH$(CH_2)_5$NHSu] NEOEOEN[Su(NPN)$_2$]Lys$_8$[Su-p-Bn-DTPA-O$^t$Bu]$_{16}$ (1 mg, yield 5%) as a white foam. HPLC/MS (Hydrophobic/TBA) Rt=7.97 min; ESI MS (+ve) m/z=16220; calc. m/z for $C_{834}H_{1375}N_{99}O_{214}$; 16216.3 g/mol.

iv. [TFA.$NH_2(CH_2)_5$NHSu]NEOEOEN[Su(NPN)$_2$] Lys$_8$[Su-p-Bn-DTPA]$_{16}$

To [BocNH$(CH_2)_5$NHSu]NEOEOEN[Su(NPN)$_2$]Lys$_8$ [Su-p-Bn-DTPA-O$^t$Bu]$_{16}$ (1 mg, 0.062 µmol) was added 20% TFA/DCM (5 mL). The solution was stirred at room temperature for 2 h. The reaction solution was concentrated in vacuo to provide [TFA.$NH_2(CH_2)_5$NHSu]NEOEOEN[Su(NPN)$_2$] Lys$_8$[Su-p-Bn-DTPA-O$^t$Bu]$_{16}$ as a foam (1 mg). HPLC/MS (Hydrophobic/TPA) no LC/MS was obtained for this compound ($C_{558}H_{820}N_{99}O_{238}$).

Example 10

NDP-α-MSH-$CH_2$CO NEOEOEN[Su(NPN)$_2$] {GlyLys[ε-Flu][α-Lys(PEG$_{570}$)$_2$}$_2$ i. HO-Su(NPN)$_2$[CBz]$_2$

A mixture of (NPN)$_2$[CBz]$_2$ (20.0 g, 0.05 mol) and succinic anhydride (6.0 g, 0.06 mol, 1.2 equivalents) in toluene (180 mL) was heated at 65° C. for 16 h. The reaction was cooled to room temperature and the white solid filtered and washed with methyl-t-butyl ether (3×100 mL) to yield the product in good yield 2334 g (94%).

ii. PNPO-Su(NPN)$_2$[CBz]$_2$

To a stirred solution of 4-nitrophenol (1.91 g, 13.7 mmol) and HO-Su(NPN)$_2$[CBz]$_2$ (13.7 mmol) in EtOAc (150 mL) was added a solution of DCC (2.97 g, 14.4 mmol) in EtOAc (50 mL) at room temperature. The mixture stirred at room temperature overnight, then filtered (to remove DCU). The mixture was then washed with $K_2CO_3$ (1.0 M), brine 1:1 (3×300 mL), dried ($MgSO_4$), filtered and concentrated, providing 7.80 g of PNPO-Su(NPN)$_2$[CBz]$_2$.

iii. [Boc]NEOEOEN[Su(NPN)$_2$][CBz]$_2$

To a solution of [Boc]NEOEOEN (3 g, 12 mmol) in 1:1 DMF/DMSO (60 mL) was added TEA (3.4 mL, 240 mmol) and a solution of PNPO-Su(NPN)$_2$[CBz]$_2$ (7.5 g, 12 mmol) in DMSO (30 mL). The solution was stirred at room temperature for 15 h. The solution was concentrated in vacuo and redissolved in water (300 mL). The aqueous solution was washed with EtOAc (3×300 mL) and the combined organic washings were dried over $Na_2SO_4$. Solvents were removed in vacuo and the crude oil purified by Silica Gel chromatography (3% MeOH/DCM) to provide [Boc]NEOEOEN[Su (NPN)$_2$][CBz]$_2$ as a colourless vicious oil (8.2 g, 93%). HPLC (Hydrophilic/TFA) Rt=9.20 min; ESI MS (+ve) 730.3 [M+1H]; calc. m/z for $C_{37}H_{55}N_5O_{10}$): 729.9.

iv. [Boc]NEOEOEN[Su(NPN)$_2$][$NH_2$]$_2$

To a solution of [Boc]NEOEOEN[Su(NPN)$_2$][CBz]$_2$ (500 mg, 0.68 mmol) in trifluoroethanol (13 mL) was added 10% w/w palladium on carbon (723 mg, 34 mmol). The suspension was stirred under an atmosphere of hydrogen at atmospheric pressure for 15 h. The suspension was then filtered though a 0.2 μm filter and the filtrate concentrated in vacuo to provide [Boc]NEOEOEN[Su(NPN)$_2$][NH$_2$]$_2$ as a clear oil (250 mg, 80%). HPLC (Hydrophilic/TFA) Rt=4.50 min. ESI MS (+ve) 462.5 [M+H]$^+$; calc. m/z for C$_{21}$H$_{43}$N$_5$O$_6$: 461.6.

v. MeO-GlyLys[ε-CBz][α-Boc]

To a stirred suspension of MeOGly.HCl (12.56 g, 0.11 mol) and DMF (200 mL) was slowly added TEA (42 mL, 0.30 mol) at room temperature. The active ester, PNPO-α-Boc-ε-CBz-Lys (50.15 g, 0.10 mol) was added to the suspension in 2-3 g portions. The bright yellow mixture was stirred at room temperature for 18 h. The volatiles were removed in vacuo and the resulting residue partitioned between EtOAc (200 mL), 10% Na$_2$CO$_3$ (100 mL) and water (175 mL). The organic layer was washed sequentially with 5% Na$_2$CO$_3$ (4×200 mL), 0.25 M HCl (3×50 mL) and brine (1×50 mL), dried (MgSO$_4$), filtered and concentrated to give the product as a colourless oil (44.39 g, 98%). HPLC (Hydrophobic/Formate) Rt=5.22 min. ESI MS (+ve) 452.02 [M+H]$^+$; calc. m/z for C$_{22}$H$_{33}$N$_3$O$_7$: 451.52.

vi. MeO-GlyLys[ε-CBz][α-NH$_2$.TFA]

To a stirred, chilled solution of MeO-GlyLys[ε-CBz][α-Boc] (43.4 g, 96.03 mmol) in acetic acid (150 mL) was added neat TFA in portions (total 170 mL). The reaction was then stirred at room temperature for 5 h. Volatiles were removed under reduced pressure; residual TEA and acetic acid were removed by azeotroping with methanol (5×200 mL). The product was obtained as a pale yellow oil (46.04 g). HPLC (Hydrophilic/Formate) 12.33 min; ESI MS (+ve) 352 [M+H]$^+$; calc. m/z for C$_{17}$H$_{25}$N$_3$O$_5$: 351.40.

vii. MeO-GlyLys[ε-CBz][α-Lys][Boc]$_2$

To a stirred solution of MeO-GlyLys[ε-CBz][α-NH$_2$.TFA] (96 mmol) in DMF (200 mL) was added TEA (33.5 mL, 0.24 mol) followed by DBL-OPNP (49.4 g, 0.106 mol). The solution was stirred at room temperature for 17 h. A solution of glycine (3.98 g, 53 mmol) in water (50 mL) was added to the crude reaction mixture and stirring was continued for 18 h further. Water (200 mL) was added and the yellow precipitate was collected by filtration, then resuspended in 5% Na$_2$CO$_3$ (200 mL); and stirred for 1.5 h. The crude product was collected by filtration and resuspended in Water (3×200 mL); the solids were collected by filtration and air dried to yield the product as a fine yellow powder (61.07 g, 94%). HPLC (Hydrophobic/Formate) Rt=7.90 min; ESI MS (+ve) 680.15 [M+H]+; calc. m/z for C$_{33}$H$_{53}$N$_5$O$_{10}$: 679.82.

viii. MeO-GlyLys[ε-CBz][α-Lys][NH$_2$.TFA]$_2$

To a stirred suspension of MeO-GlyLys[ε-CBz][α-Lys][Boc]$_2$ (4 g, 7.36 mmol) in acetic acid (15 mL) at 0° C. was added TEA (15 mL), dropwise. The mixture was allowed to warm to room temperature and was stirred at room temperature overnight. The solvents were removed and the residue dissolved in water (100 mL) and filtered. The filtrate was lyophilized to give a colourless oil (4.4 g). HPLC/(Hydrophilic/TEA) Rt=5.03 min; ESI MS (+ve)=480 [M+H]$^+$; calc. m/z for C$_{23}$H$_{37}$N$_5$O$_6$: 479.5.

ix. MeO-GlyLys[ε-CBz][α-Lys][PEG$_{570}$]2

To a stirred suspension of MeO-GlyLys[ε-CBz][α-Lys][NH$_2$.TFA]$_2$ (735 mg, 1.04 mmol) in DMF (anhydrous, 20 mL) was added. TEA (1.5 mL, 5 equivalents per amine) followed by a solution of m-dPEG$_{570}$-NHS (1.5 g, 1.05 equivalents per amine) in DMF (10 mL). The mixture was stirred at room temperature overnight. The solvents were removed and the residue purified on a column of silica gel (0.063-0.04 mm, eluents 7%~30% MeOH/DCM) to give the desired product as a colourless oil (1.0 g). HPLC (Hydrophilic/TFA) Rt=7.87 min; ESI MS (+ve) 828 [M+2×NH$_4$]$^{2+}$, 811 [M+2H]$^{2+}$, 541 [M+3H]$^{3+}$; calc. m/z for C$_{75}$H$_{137}$N$_5$O$_{32}$: 1620.9.

x. HO-GlyLys[ε-CBz][α-Lys][PEG$_{570}$]$_2$

To a stirred suspension of MeO-GlyLys[ε-CBz][α-Lys][PEG$_{570}$]$_2$ (1.0 g, 0.62 mmol) in THF (20 mL) was added 1M LiOH (2 mL). The mixture was stirred at room temperature for 3 h; followed by acidification with 1 M HCl to pH 6. The solvents were removed and the residue dissolved in water and lyophilized to give the product as a colourless solid. HPLC (Hydrophilic/TFA) Rt=7.61 min; ESI MS (+ve) 821 [M+(2×NH$_4$)]$^{2+}$, 804 [M+2H]$^{2+}$, 536 [M+3H]$^{3+}$; calc. m/z for C$_{74}$H$_{135}$N$_5$O$_{32}$: 1606.9.

xi. [Boc]NEOEOEN[Su(NPN)$_2$][GlyLys]$_2$[ε-CBz]$_2$[Lys]$_2$[PEG$_{570}$]$_4$

To a stirred solution of [Boc]NEOEOEN[Su(NPN)$_2$][NH$_2$]$_2$ (Example 11iv) (100 mg, 0.22 mmol) and HO-GlyLys[ε-CBz][α-Lys][PEG$_{570}$]$_2$ (700 mg, 0.44 mmol) in DMF (anhydrous, 9 mL) at 0° C., was added PyBop (250 mg) and DIPEA (160 μL). The mixture stirred at room temperature overnight. Volatiles were removed under reduced pressure to give a residue which was chromatographed on a silica gel column (0.063-0.04 mm, eluants 10%-30% MeOH/DCM), to give 600 mg the product as a colourless oil. HPLC (Hydrophilic/TFA) Rt=9.18 min; ESI MS (+ve) 886 [M-Boc+4H]$^{4+}$, 729 [M+5H]$^{5+}$, 709 [M-Boc+5H]$^{5+}$; data deconvoluted using transform calculation to give 3638.9[M+H]$^+$; calc. m/z for C$_{169}$H$_{309}$N$_{15}$O$_{68}$: 3639.3.

xii. [Boc]NEOEOEN[Su(NPN)$_2$][GlyLys]$_2$[ε-NH$_2$]$_2$[Lys]$_2$[PEG$_{570}$]$_4$ To a stirred solution of [Boc]NEOEOEN[Su(NPN)$_2$][GlyLys]$_2$[ε-CBz]$_2$[Lys]$_2$[PEG$_{570}$]$_4$ (20 mg, 5.5 μmol) in trifluoroethanol (1.0 mL) was added 10% w/w palladium on carbon (20 mg, 9.4 μmol). The suspension was stirred under hydrogen at atmospheric pressure for 15 h. The suspension was then filtered through a 0.2 micron filter and the filtrate reduced in vacuo to provide the product as a clear viscous oil, (15 mg, 81%). HPLC (Hydrophilic/TPA) Rt=7.50 min; ESI MS (+ve) 1130.4 [M+3H]$^{3+}$, 843.7 [M+4H]$^{4+}$, 675.1 [M+5H]$^{5+}$; data deconvoluted using transform calculation to give 3371.0; calc. m/z for C$_{153}$H$_{297}$N$_{15}$O$_{64}$: 3371.1.

xiii. [Boc]NEOEOEN[Su(NPN)$_2$][GlyLys]$_2$[ε-Fluorescein]$_2$[Lys]$_2$[PEG$_{570}$]$_4$ To a stirred solution of [Boc]NEOEOEN[Su(NPN)$_2$][GlyLys]$_2$[ε-NH$_2$]$_2$[Lys]$_2$[PEG$_{570}$]$_4$ (25 mg, 60 μmol) and TEA (25 μL) in DMF (anhydrous, 8 mL) was added fluorescein N-hydroxysuccinimidyl ester (9 mg, 1.25 equivalents per amine). The mixture was stirred for 2 h at room temperature. Volatiles were removed to give a residue; from which the product was purified by HPLC (ammonium formate buffer). HPLC (Hydrophilic/TFA) Rt=8.71 min; ESI MS (+ve) 1023 [M+4H]$^{4+}$, 819 [M+5H]$^{5+}$, 682 [M+6H]$^{6+}$; date deconvoxiv. [TFA.NH$_2$]EOEOEN[Su(NPN)$_2$][GlyLys]$_2$ [ε-Fluorescein]$_2$[Lys]$_2$[PEG$_{570}$]$_4$ A suspension of [Boc]NEOEOEN[Su(NPN)$_2$][GlyLys]$_2$ [ε-Fluorescein]$_2$[Lys]$_2$[PEG$_{570}$]$_4$ (1 mg, 0.25 μmol) was suspended in 20% TFA/DCM (1 mL) and stirred at room temperature for 1 h. The volatiles were removed to provide the product. HPLC (Hydrophilic/TFA) Rt=8.13 min; ESI MS (+ve) 1330 [M+3H]$^{3+}$, 998 [M+4H]$^{4+}$, 798 [M+5H]$^{5+}$; data deconvoluted using either MaxEnt or Transform calculation to give 3987; calc. m/z for $C_{190}H_{309}N_{15}O_{74}$: 3987.5.

xv. MAL-(CH$_2$)$_2$CO NEOEOEN[Su(NPN)$_2$] [GlyLys]$_2$[ε-Fluorescein]$_2$[Lys]$_2$[PEG$_{570}$]$_4$ To a stirred solution of [TFA.NH$_2$]EOEOEN[Su(NPN)$_2$] [GlyLys]$_2$[ε-Fluorescein]$_2$[Lys]$_2$[PEG$_{570}$]$_4$ (14 mg, 3.4 μmol) DMF (5 mL) was added TEA (100 μL, 0.73 mmol) and 3-maleimidopropionic acid N-hydroxysuccinimide ester (20 mg, 75 μmol). The reaction solution was stirred for 16 h. The solution were evaporated in vacuo to give a crude mixture, which was purified by HPLC to give MAL-(CH$_2$)$_2$CO NEOEOEN[Su(NPN)$_2$][GlyLys]$_2$[ε-Fluorescein]$_2$[Lys]$_2$ [PEG$_{570}$]$_4$ (0.7 mg). HPLC/MS (Hydrophilic/TPA) Rt=8.40 min; ESI MS (+ve)=4140; calc. m/z for $C_{197}H_{314}N_{16}O_{77}$: 41383.1.

xvi. NDP-α-MSH-MAL-(CH$_2$)$_2$CO NEOEOEN[Su (NPN)$_2$][GlyLys]$_2$[ε-Fluorescein]$_2$[Lys]$_2$[PEG$_{570}$]$_4$ To the peptide (3-mercapto-NDP-α-MSH, 3-mercapto-Ser-Tyr-Ser-Nle-His-DPhe-Arg-Trp-Gly-Lys-Pro-Val-NH$_2$, 1 mg, 0.59 μmol) was added a freshly prepared solution of MAL-(CH$_2$)$_2$CO NEOEOEN[Su(NPN)$_2$][GlyLys]$_2$[ε-Fluorescein]$_2$[Lys]$_2$[PEG$_{570}$]$_4$ (50 μg, 0.012 μmol) in buffer (pH 8.4, 0.1 M Na$_2$HPO$_4$/0.1 M HCl, 0.5 mL). The mixture was stirred at room temperature for 3 h. The reaction mixture was analyzed by HPLC/MS (Hydrophilic/TFA) Rt=9.03 min; ESI MS (+ve) 5830 ([M+H]$^+$); calc. for $C_{276}H_{428}N_{38}O_{95}S$: 5830.6.

Example 11

Single chain antibody-MAL-(CH$_2$)$_2$CO NEOEOEN[Su (NPN)$_2$][GlyLys]$_2$[ε-Fluorescein]$_2$[Lys]$_2$[PEG$_{570}$]$_4$ To an excess of the single chain antibody in buffer (pH 8.4, 0.1 M Na$_2$HPO$_4$/0.1 M HCl) could be added a freshly prepared solution of MAL-(CH$_2$)$_2$CO NEOEOEN [Su(NPN)$_2$] [GlyLys]$_2$[ε-Fluorescein]$_2$[Lys]$_2$[PEG$_{570}$]$_4$, after reaction for several hours the dendrimer-antibody fragment construct could be detected by SDS-PAGE.

Example 12

Mutation of Single-Chain Antibodies with Q-Tag

The antibody was prepared as described in international Application No. PCT/AU2006/000943.

Introduction of a Transglutaminase recognition tag (Q2-tag) (Lin C.-W., Ting, A, Y. *J. Am. Chem. Soc.* 2006 128, 4542-4543) was performed by standard molecular biology methods either at the C-terminus after the His tag (Sequence: . . . RTGHHHHHHGGAPKPQQFM) or at the N-terminus after the leading sequence (Sequence: SPK-PQQFMGGGSGGGSAMAQVQLQ . . . ). The identity of the clones were confirmed by sequencing.

Transglutaminase Reaction

Antibody with a C-terminal Q2-tag (75 μL, 1.5 nmol) in Tris-HCl buffer (0.1 M, pH 7.5, 10 mM CaCl$_2$) was mixed with either N-Fluorescein cadaverine, Example 8 (10 μL, 1 mM final concentration) or Example 9iv (1 mM final concentration) and 15 μL guinea pig liver transglutaminase (final concentration 0.05 U). Reactions were performed at room temperature overnight to allow labelling.

Analysis of the Transglutaminase Reaction Products

Example 8 coupled to the antibody was analysed by flow cytometry on activated and non activated platelets (detailed procedure below). The results from this experiment clearly show exclusive binding to the activated platelets as expected.

Example 9iv coupled to the antibody was loaded with Gadolium, dialysed and imaged on human thrombi in MRI (detailed procedure below). The results from this experiment show that the surface of the human thrombi had a bright T1 weighted Gadolium MRI signal and indicated successful binding of Gadolium loaded dendrimer via antibodies targeting activated platelets. The absence of stain inside the thrombi confirmed the selectively of the Gadolium labelling event.

A control experiment where the antibody was incubated with Example 9iv but without the Transglutaminase coupling enzyme did not show any MRI signal.

Mutation of Single-Chain Antibodies with C-Terminal Cysteine

The antibody was prepared as described in International Application No. PCT/AU2006/000943.

Antibodies were mutated by standard molecular biology methods to generate a C-terminal cysteine after the His tag (sequence . . . RTGHHHHHHGGAC). The identity of the clone was confirmed by sequencing.

Preparation of C-Terminal Cysteine Single Chain Antibody Prior to Coupling Reaction Before coupling a selective mild reduction with dithiolthreitol (2 mM, final concentration) was performed in degassed nitrogen saturated Nellis Buffer (10 mM Na-phosphate buffer, 0.2 mM EDTA, 30 mM NaCl, pH 6.7) under nitrogen atmosphere. Excess dithiolthreitol was removed by dialysis (10,000 Dalton dialysis membrane, 6 h against 500 ml Nellis buffer with 3 buffer changes every 2 h) under nitrogen.

Coupling Reaction of C-Terminal Cysteine Single Chain Antibody with Example 7v

Single-Chain antibody with free cysteine (1 nmol) in 30 μL degassed nitrogen saturated Nellis Buffer (10 mM Na-phosphate buffer, 0.2 mM EDTA, 30 mM NaCl, pH 6.7) was mixed with 5 nmol of Example 7v at room temperature for 1 h under nitrogen. Unreacted maleimide groups were inactivated by incubation with 0.5 mmol cysteine for 15 min at room temperature. Non conjugated single-chain antibody and unreacted free maleimide containing substrates were removed by size exclusion chromatography. Final products were loaded with Gadolium and analysed by staining human thrombi followed by MR imaging (see detailed procedure below).

Coupling Reaction of C-Terminal Cysteine Single Chain Antibody with Example 6

Single-Chain antibody with free cysteine (1 nmol) could be coupled in a similar manner to the example directly above using Example 6.

Analysis of C-Terminal Cysteine Single Chain Antibody with Example 7v

Analysis by MRI of the antibody—Example 7v fusion product show that the surface of the human thrombi had a bright T1 weighted Gadolium MRI signal and indicated successful binding of Gadolimn loaded dendrimer via antibodies targeting activated platelets. The absence of stain inside the thrombi confirmed the selectively of the Gadolium labelling event.

A control experiment where non reduced antibody was incubated with Example 7v did not show any MRI signal.

Preparation of Traut's Reagent Modified Single Chain Antibody Prior to Coupling Reaction Traut's modification of the single chain antibody was performed for 1 h at room temperature by adding 1:1, 1:2, 1:5 and 1:10 equivalents of Traut's reagents (2-Iminothiolane-HCl) in degassed nitrogen saturated Nellis Buffer (10 mM Na-phosphate buffer, 0.2 mM EDTA, 30 mM NaCl, pH 6.7) to generate free thiol groups at surface available lysine residues.

Coupling Reaction of Thiol Functionalised Antibodies with Various Maleimide Containing Reagents Single-Chain antibody with free thiols (1 mmol) in 30 µL degassed nitrogen saturated Nellis Buffer (10 mM Na-phosphate buffer, 0.2 mM EDTA, 30 mM NaCl, pH 6.7) was mixed with 1-5 nmol of maleimide containing substrates [either 2 KDa trident PEG, 20 KDa linear PEG or Example 7v] at room temperature for 1 h under nitrogen. Unreacted maleimide groups were inactivated by incubation with 0.5 mmol cysteine for 15 min at room temperature. Non conjugated single-chain antibody and unreacted free maleimide containing substrates were removed by size exclusion chromatography. Coupling was confirmed by SDS-PAGE and Western Blot (see detailed procedure below). Final products were loaded with Gadolium and analysed by flow cytometry on activated platelets for binding and by staining human thrombi followed by MR imaging (see detailed procedure below).

Analysis of Thiol Functionalised Antibodies

Analysis by SDS PAGE with increasing molar concentration of Traut's reagent (single chain antibody/Traut's Reagent; 1:1, 1:2, 1:5, 1:10 ratio), followed by subsequent reaction with either 2 KDa trident PEG, 20 KDa PEG or Example 7v, showed a higher proportion of higher molecular weight constructs. For the fusion product made using the dendrimer, Example 7v, the entire starting antibody was consumed producing only higher molecular weight constructs. This was in line with our expectations.

Further evidence for the antibody—Example 7v fusion construct was obtained by Western Blot analysis, which as expected proved that the higher molecular weight construct observed in the SDS PAGE was indeed the fusion product.

The antibody—Example 7v fusion product was further characterised by flow cytometry in order to determine if the antibody was still functional. Analysis of the binding with both activated and non-activated platelets (detailed procedure below), showed that the construct was still active and exclusively bound activated platelets.

Finally, MRI analysis of the antibody—Example 7v fusion product, showed that the surface of the human thrombi had a bright T1 weighted Gadolimn MRI signal and indicated successful binding of Gadolium loaded dendrimer via antibodies targeting activated platelets. The absence of stain inside the thrombi confirmed the selectively of the Gadolium labelling event.

A control experiment where non-modified antibody was incubated with Example 7v did not show any MRI signal.

Standard Gadolinium Loading of Antibody-Dendrimer Fusion Constructs

Antibody-Dendrimer constructs (1.5 nmol) were loaded with Gadolinium by adding 64 nmol $GdCl_3.6H_2O$ in PBS (0.1M, pH 7.4) overnight at room temperature under shaking. Excess Gadolinium was removed by dialysis (10,000 Dalton dialysis membrane, 12 h against 500 mL PBS with 3 buffer changes every 4 h).

Standard Staining of In Vitro Formed Human Plasma Thrombi

To form human thrombi in vitro 1 mL platelet rich plasma (citrated blood spun down at 1000 rpm for 10 min) was mixed with 100 µL ADP, 88 µL Actin, 25 µL 1 M $CaCl_2$ in a 1.5 mL reaction tube. Samples were incubated for 12 min at 37° C. in a water bath, incubated with antibody-dendrimer fusion product for another 30 min at 37° C. under continuous rotation. Thrombi were washed 3 times with 2 mL PBS for 10 min and fixed in formalin solution (1%) before imaging.

Standard MRI Imaging Procedure

MRI of thrombi was performed on a 4.7 Tesla animal MRI scanner (Biospin Bruker). T1 weighted images with TE/TR 15 ms/350 ms were taken with a resolution of 512×512 µm (FOV 7 cm, average 4). 10 slices of 1 mm thickness were taken.

Standard Flow Cytometry Conditions

Human citrated whole blood was diluted 1/50 in modified Tyrode's buffer, either activated by addition of 20 µM ADP or non-activated and then pre-incubated for 10 min with 5 lag/mL single-chain-dendrimer product. Cadaverine addition products were detected by the FITC signal of the cadaverine, single-chain antibodies were detected by a secondary antibody (Penta His Alexa Fluor 488 Conjugate) directed against the Histidine(6)-tag of the single chain antibody. Samples were measured in a FACSCalibur flow cytometer after fixation with CellFIX.

SDS-PAGE and Western Blotting Under Reducing Conditions

Proteins and protein-dendrimer fusion products were separated on a 12% SDS-PAGE gel and transferred onto an Immobilon P membrane for immunoblotting. After blocking the membrane overnight with phosphate buffered saline containing 0.2% Tween 20 (PBS-Tween) and 1% BSA, a HRP-labelled anti-His(6)-antibody was added (dilution 1:500) and incubated for 2 h at room temperature. The membrane was washed several times with PBS-Tween buffer before visualization of peroxidase activity by addition of peroxidase substrate.

The invention claimed is:

1. A macromolecule comprising:
   a dendrimer comprising
   (i) a core moiety having a first amino nitrogen atom for attachment to a first functional moiety and at least two further amino nitrogen atoms for attachment to lysine or lysine analogue building units; wherein the core is selected from the group consisting of a tri-amino compound, a tetra-amino compound, and a penta-amino compound; and
   (ii) at least one layer of lysine or lysine analogue building units, wherein each building unit in a first of the layers is attached to the core moiety by an amide bond, through the at least two further amino nitrogen atoms of the core moiety, and any building units in subsequent layers are attached to a previous layer through an amide bond, wherein an outermost layer of the at least one layer of lysine or lysine analogue building units has at least one surface amine for attachment to the one or more second functional moieties; and
   a first functional moiety attached to the core moiety through the first amino nitrogen atom;
   one or more second functional moieties attached to the surface amino nitrogen atoms of the outermost layer of lysine or lysine analogue building units;
   wherein the first functional moiety is a targeting molecule, which retains the ability in said macromolecule to specifically bind to another molecule, and the second functional moiety is a signalling entity.

2. A macromolecule according to claim 1 wherein the building units are selected from:

Lysine 1 having the structure:

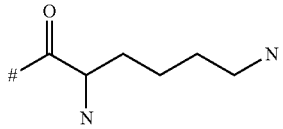

1

Glycyl-Lysine 2 having the structure:

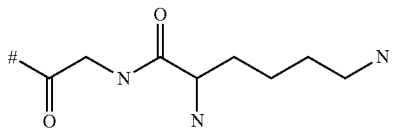

2

Analogue 3, having the structure below, where a is an integer 1 or 2; and b and c are independently integers 1, 2, 3 or 4

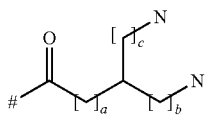

3

Analogue 4, having the structure below, where a is an integer 0, 1 or 2; and b and c are independently integers 2, 3, 4, 5 or 6

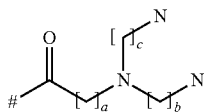

4

Analogue 5, having the structure below, where a is an integer 0, 1, 2, 3, 4 or 5; and b and c are independently integers 1, 2, 3, 4 or 5

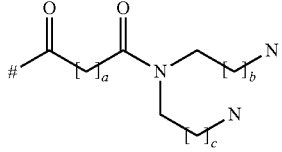

5

Analogue 6, having the structure below, where a is an integer 0, 1, 2, 3, 4 or 5; and b and c are independently integers 0, 1, 2, 3, 4 or 5

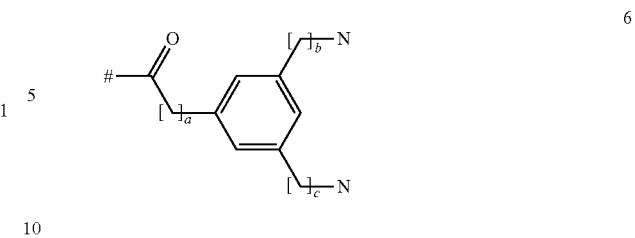

6

Analogue 7, having the structure below, where a is an integer 0, 1, 2, 3, 4 or 5; and b and c are independently integers 1, 2, 3, 4 or 5

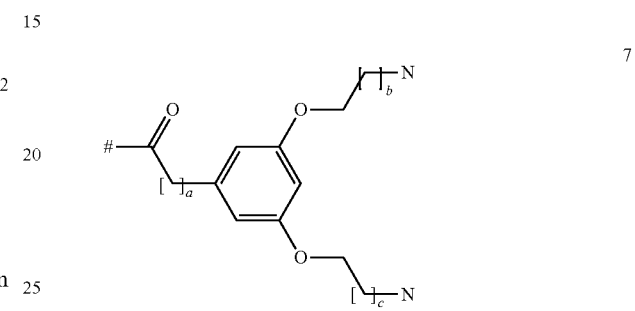

7

Analogue 8, having the structure below, where a is an integer 0, 1, 2, 3, 4 or 5; and b, c and d are independently integers 1, 2, 3, 4 or 5

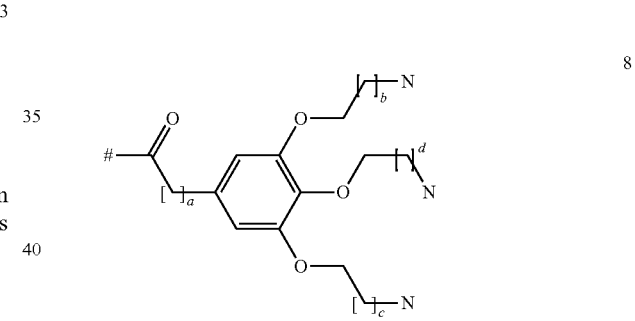

8

Analogue 9, having the structure below, where a is an integer 0, 1, 2, 3, 4 or 5; and b and c are independently integers 1, 2, 3, 4 or 5

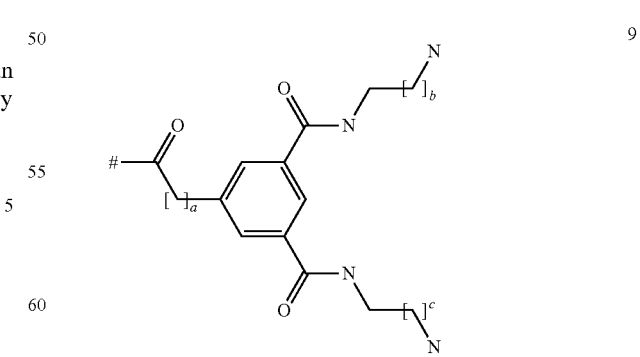

9 wherein # indicates a carboxyl group bonded as an amide to an amine of the core or a lysine building unit, and wherein any methylene group of the building units may be replaced by a methyleneoxy ($CH_2$—O) or ethyleneoxy (CH₂—CH₂—O) group, provided that this does not result in the formation of a carbonate (—O—C(O)—O—) or carbamate (—O—C(O)—N—) moiety within the building unit.

3. A macromolecule according to claim 2 wherein the building units are selected from Lysine 1, Glycyl-Lysine 2 and Lysine analogue 5:

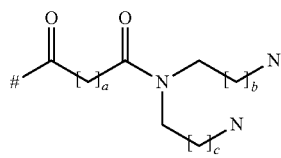

5 where a is an integer 0, 1 or 2 and wherein any methylene group of 1, 2 or 5 may be replaced by a methyleneoxy or ethyleneoxy group provided that this does not result in the formation of a carbonate or carbamate moiety within the building unit.

4. A macromolecule according to claim 1 wherein the core is a tri-amino compound resulting from the reaction of lysine, or a lysine analogue, with one amino nitrogen atom of a di-amino compound selected from:

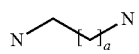

10 where a is an integer of 1 to 9;

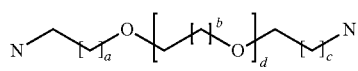

11 where a, b and c, are independently integers 1, 2, 3, 4 or 5; and d is an integer from 0-100;

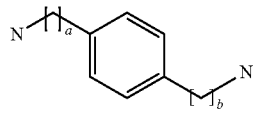

12 where a and b, are independently integers 0, 1, 2, 3, 4 or 5;

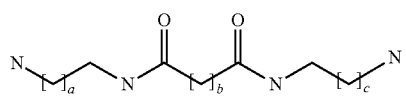

13 where a and c, are independently integers 1, 2, 3, 4, 5 or 6 and where b is an integer from 0, 1, 2, 3, 4, 5 or 6;

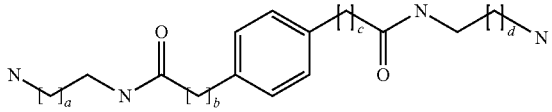

14 where a and d, are independently integers 1, 2, 3, 4, 5 or 6 and where b and c, are independently integers 0, 1, 2, 3, 4, 5 or 6.

5. A macromolecule according to claim 4 wherein the di-amino compound is selected from the following:

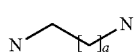

10 where a is an integer 1, 2, 3, 4 or 5;

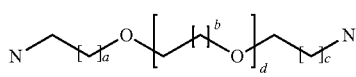

11 where a, b and c, are independently integers of 2 or 3 and d is an integer from 1-30;

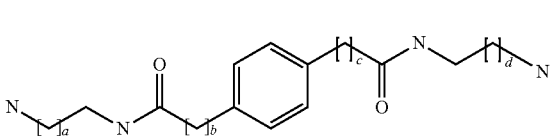

14 where a and d, are independently integers of 1 or 2 and where b and c, are independently integers from 0, 1 or 2.

6. A macromolecule according to claim 5 wherein the core is derived from compound 11, wherein a, b, c and d are each 1 and analogue 5

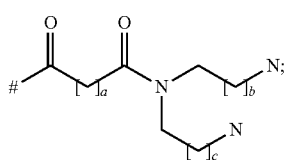

5 wherein each of a, b and c are 2.

7. A macromolecule according to any one of claims 1 to 4 wherein the core is
   (i) a tri-amino or tetra-amino compound, or
   (ii) a tetra-amino or penta-amino compound resulting from the reaction of a lysine or a lysine analogue with one amino nitrogen atom of a tri-amino or tetra-amino compound;

wherein the tri-amino and tetra-amino compounds are selected from the group consisting of:

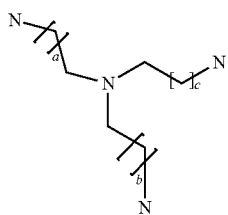
15
where a, b and c, are independently integers 1, 2, 3, 4, 5 or 6;
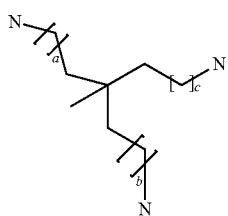
16
where a, b and c, are independently integers 0, 1, 2, 3, 4, 5 or 6;
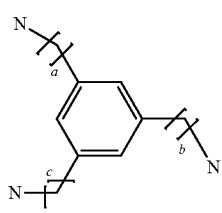
17
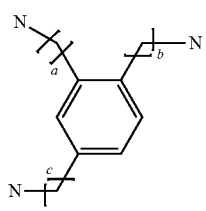
18
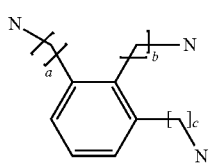
19
where a, b and c, are independently integers 0, 1, 2, 3, 4, 5 or 6;
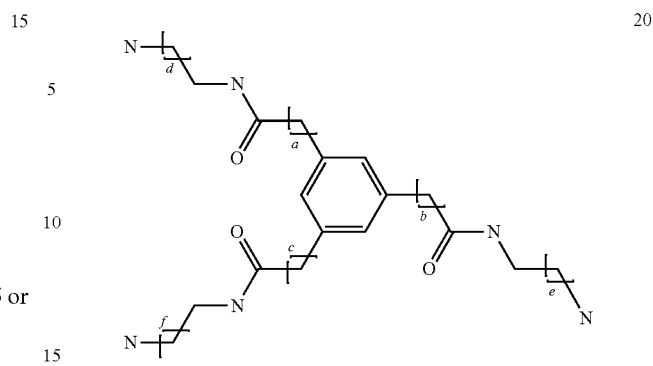
20
where a, b and c, are independently integers 0, 1, 2, 3, 4, 5 or 6; and d, e and f, are independently integers 1, 2, 3, 4, 5 or 6,
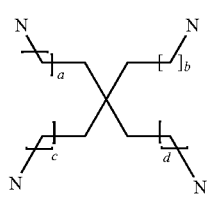
21
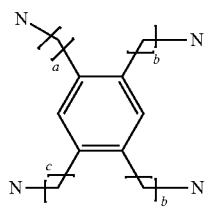
22
where a, b, c and d, are independently integers 0, 1, 2, 3, 4, 5 or 6
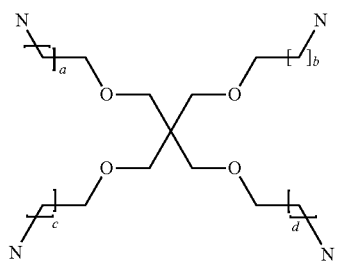
23
where a, b, c and d, are independently integers 1, 2, 3, 4, 5 or 6

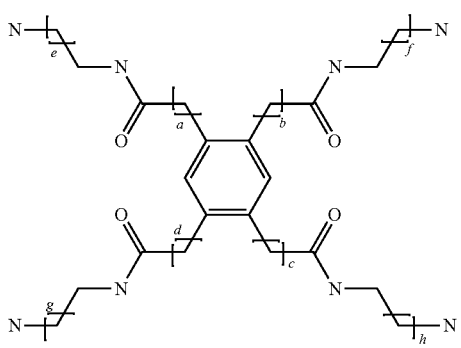

24 where a, b, c and d, are independently integers 0, 1, 2, 3, 4, 5 or 6; and e, f, g and h, are independently integers 1, 2, 3, 4, 5 or 6.

8. A macromolecule according to claim 7 wherein the tri-amino or tetra-amino compound is selected from:

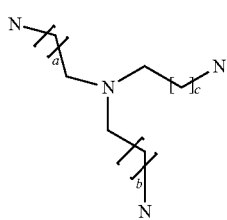

15 where a, b and c, which may be the same or different, are integers of 1 to 2;

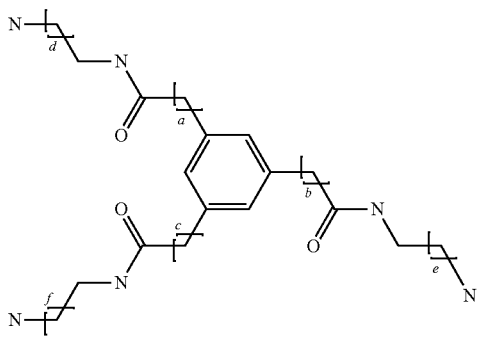

20 where a, b and c, are independently integers 0, 1 or 2; and d, e and f, are independently integers 1 or 2, or a tetra-amino compound is selected from the group consisting of:

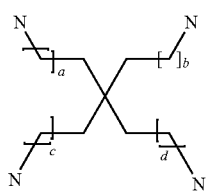

21 where a, b, c and d, are independently integers 0 or 1

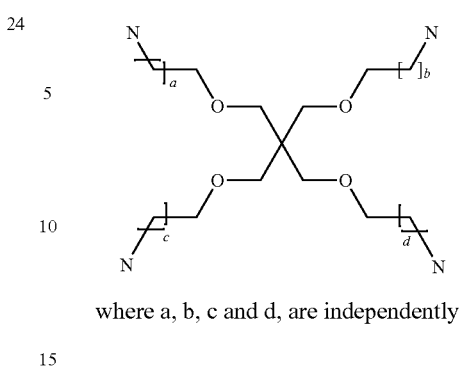

23 where a, b, c and d, are independently integers 1 or 2;

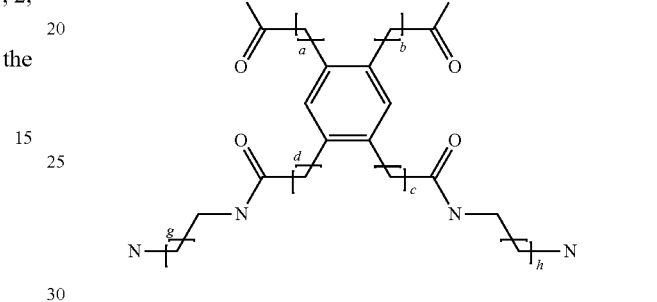

24 where a, b, c and d, are independently integers 0, 1 or 2; and e, f, g and h, are independently integers 1 or 2.

9. A macromolecule according to claim 1 comprising 1, 2, 3, 4 or 5 layers of building units.

10. A macromolecule according to claim 9 comprising 2, 3 or 4 layers of building units.

11. A macromolecule according to claim 1 further comprising at least one third functional moiety on the surface.

12. A macromolecule according to claim 1 wherein each surface amino nitrogen atom is attached to a functional moiety.

13. A macromolecule according to claim 1 further comprising a third functional moiety which is a targeting molecule the same as or different to the first targeting molecule.

14. A macromolecule according to claim 1 wherein the targeting molecule is an antibody.

15. A macromolecule according to claim 14 wherein the antibody is capable of binding to activated platelets, activated leukocytes, fibrin or activated endothelial cells.

16. A macromolecule according to claim 15 wherein the targeting molecule targets Mac-1.

17. A macromolecule according to claim 16 wherein the antibody is a single chain antibody which includes one or more of the following regions: HCDR1, HCDR2, HCDR3, LINKER, LCDR1, LCDR2 or LCDR3.

18. The macromolecule according to claim 1 wherein the signalling entity comprises a paramagnetic entity.

19. The macromolecule according to claim 18 wherein the paramagnetic entity is $Fe^{3+}$, $Mn^{2+}$ or $Gd^{3+}$.

20. The macromolecule according to claim 19 wherein the paramagnetic entity is $Gd^{3+}$.

21. The macromolecule according to claim 19 wherein the paramagnetic entity is attached to a nitrogen atom through a chelant.

22. A macromolecule according to claim 1 wherein one or more functional moieties are attached to the core or surface amino nitrogen atoms via a linker.

23. A macromolecule according to claim 22 wherein the linker is a polyethylene glycol linker having from 1 to 100 repeat units.

24. A macromolecule according to claim 1 wherein a first core or surface nitrogen atom, and/or any linker and/or the functional moiety is modified by a modifier group to facilitate attachment.

25. A macromolecule according to claim 24 wherein the modifier group may be selected from maleimide, haloacetamide, hydrazide, alkoxyamine or 3-(2-pyridyldithio)propionate.

26. A composition comprising a macromolecule according to claim 1 and at least one pharmaceutically acceptable excipient, carrier or adjuvant therefor.

27. A method for imaging, such as magnetic resonance imaging, of a cellular target in a mammal, the method including the steps of
   (a) administering to a mammal an imaging agent comprising the macromolecule according to claim 1;
   (b) allowing the imaging agent to bind to the cellular target; and
   (c) imaging the mammal to generate an image.

28. A macromolecule according to claim 4 wherein the di-amino compound is

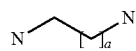

where a is an integer of 1, 2, 3, 4 or 5.

29. A macromolecule according to claim 4 wherein the di-amino compound is:

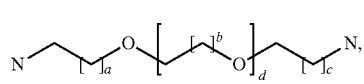

wherein a, b and c are independently integers 2 or 3.

30. A macromolecule according to claim 4 wherein the di-amino compound is

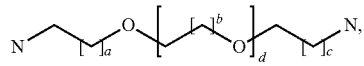

wherein d is an integer from 1 to 30.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial
<220> FEATURE:
<223> OTHER INFORMATION: synthetic peptide of Mac-1 targeting molecule

<400> SEQUENCE: 1
```

```
Asp Ser Thr Leu Ala Pro Ile Phe Glu Tyr
1               5                   10

<210> SEQ ID NO 2
<211> LENGTH: 10
<212> TYPE: PRT
<213> ORGANISM: Artificial
<220> FEATURE:
<223> OTHER INFORMATION: synthetic peptide of Mac-1 targeting molecule

<400> SEQUENCE: 2

Asp Leu Trp Gly Phe Gln Leu Phe Asp Tyr
1               5                   10

<210> SEQ ID NO 3
<211> LENGTH: 8
<212> TYPE: PRT
<213> ORGANISM: Artificial
<220> FEATURE:
<223> OTHER INFORMATION: synthetic peptide of Mac-1 targeting molecule

<400> SEQUENCE: 3

Asp Phe Trp Gly Ser Tyr Asp Tyr
1               5

<210> SEQ ID NO 4
<211> LENGTH: 13
<212> TYPE: PRT
<213> ORGANISM: Artificial
<220> FEATURE:
<223> OTHER INFORMATION: synthetic peptide of HCDR1 region

<400> SEQUENCE: 4

Ala Ala Ser Gly Phe Ile Phe Arg Asp Tyr Asp Met Asp
1               5                   10

<210> SEQ ID NO 5
<211> LENGTH: 11
<212> TYPE: PRT
<213> ORGANISM: Artificial
<220> FEATURE:
<223> OTHER INFORMATION: synthetic peptide of HCDR1 region

<400> SEQUENCE: 5

Ala Ala Ser Gly Phe Ser Asn Tyr Gly Ile His
1               5                   10

<210> SEQ ID NO 6
<211> LENGTH: 10
<212> TYPE: PRT
<213> ORGANISM: Artificial
<220> FEATURE:
<223> OTHER INFORMATION: synthetic peptide of HCDR2 region

<400> SEQUENCE: 6

Thr Ser Ser Tyr Thr Ile Gln Asp Ala Ala
1               5                   10

<210> SEQ ID NO 7
<211> LENGTH: 15
<212> TYPE: PRT
<213> ORGANISM: Artificial
<220> FEATURE:
<223> OTHER INFORMATION: synthetic peptide of HCDR2 region

<400> SEQUENCE: 7
```

Val Ala Leu Ile Ser Tyr Asp Asn Gly Asn Lys Lys Phe Tyr Ala
1               5                   10                  15

<210> SEQ ID NO 8
<211> LENGTH: 10
<212> TYPE: PRT
<213> ORGANISM: Artificial
<220> FEATURE:
<223> OTHER INFORMATION: synthetic peptide of HCDR3 region

<400> SEQUENCE: 8

Asp Leu Trp Gly Phe Gln Leu Phe Asp Tyr
1               5                   10

<210> SEQ ID NO 9
<211> LENGTH: 8
<212> TYPE: PRT
<213> ORGANISM: Artificial
<220> FEATURE:
<223> OTHER INFORMATION: synthetic peptide of HCDR3 region

<400> SEQUENCE: 9

Asp Phe Trp Gly Ser Tyr Asp Tyr
1               5

<210> SEQ ID NO 10
<211> LENGTH: 10
<212> TYPE: PRT
<213> ORGANISM: Artificial
<220> FEATURE:
<223> OTHER INFORMATION: synthetic peptide of HCDR3 region

<400> SEQUENCE: 10

Asp Ser Thr Leu Ala Pro Ile Phe Glu Tyr
1               5                   10

<210> SEQ ID NO 11
<211> LENGTH: 12
<212> TYPE: PRT
<213> ORGANISM: Artificial
<220> FEATURE:
<223> OTHER INFORMATION: synthetic peptide of LINKER region

<400> SEQUENCE: 11

Lys Leu Glu Glu Gly Glu Gly Ser Glu Ala Arg Val
1               5                   10

<210> SEQ ID NO 12
<211> LENGTH: 11
<212> TYPE: PRT
<213> ORGANISM: Artificial
<220> FEATURE:
<223> OTHER INFORMATION: synthetic peptide of LCDR1 region

<400> SEQUENCE: 12

Gly Gly Asn Asn Ile Gly Ser Lys Ser Val His
1               5                   10

<210> SEQ ID NO 13
<211> LENGTH: 11
<212> TYPE: PRT
<213> ORGANISM: Artificial
<220> FEATURE:
<223> OTHER INFORMATION: synthetic peptide of LCDR1 region

<400> SEQUENCE: 13

Gly Gly Asn Asn Ile Gly Ser Thr Thr Val His

<210> SEQ ID NO 14
<211> LENGTH: 7
<212> TYPE: PRT
<213> ORGANISM: Artificial
<220> FEATURE:
<223> OTHER INFORMATION: synthetic peptide of LCDR2 region

<400> SEQUENCE: 14

Tyr Asp Ser Val Arg Pro Ser
1               5

<210> SEQ ID NO 15
<211> LENGTH: 7
<212> TYPE: PRT
<213> ORGANISM: Artificial
<220> FEATURE:
<223> OTHER INFORMATION: synthetic peptide of LCDR2 region

<400> SEQUENCE: 15

Asp Asp Asn Glu Arg Pro Ser
1               5

<210> SEQ ID NO 16
<211> LENGTH: 11
<212> TYPE: PRT
<213> ORGANISM: Artificial
<220> FEATURE:
<223> OTHER INFORMATION: synthetic peptide of LCDR3 region

<400> SEQUENCE: 16

Gln Val Trp Asp Ser Asn Thr Asp His Tyr Val
1               5                   10

<210> SEQ ID NO 17
<211> LENGTH: 11
<212> TYPE: PRT
<213> ORGANISM: Artificial
<220> FEATURE:
<223> OTHER INFORMATION: synthetic peptide of LCDR3 region

<400> SEQUENCE: 17

Gln Val Trp Asp Ser Gly Ser Asp His Val Val
1               5                   10

<210> SEQ ID NO 18
<211> LENGTH: 922
<212> TYPE: DNA
<213> ORGANISM: Artificial Sequence
<220> FEATURE:
<223> OTHER INFORMATION: C terminal Cystein sequence
      (pMT/BiP/V5-His M-LtBS-C)

<400> SEQUENCE: 18
tatgaagtta tgcatattac tggccgtcgt ggcctttgtt ggcctctcgc tcgggagatc      60
ggccatggcg caggtgcagc tgcagcagtc tggggaggc ttagtgaagc ctggagggtc      120
cctgaaactc tcctgcgcag cctctggatt cactttcagt agctatatca tgtcttgggt      180
tcgccagact ccgagaaga ggctggagtg gtcgcaacc attagaagtg gtggtgataa       240
cacctactat ccagacagtg tgaagggtcg attcaccatc tccagagaca atgccaagaa      300
caagttgtac ctgcaaatga gcagtctgag gtctgaggac acggccttgt attactgtgc      360
aatctactat ggtaactacg gggggcttgc ttactggggc caagggactc tggtcactgt      420

```
ctctgcagcc aaaacgacac ccaagcttga agaaggtgaa ttttcagaag cacgcgtaga    480
tatcttgatg acccaatctc cagcctccct atctgcatct gtgggagaaa ctgtcaccat    540
cacatgtcga gcaagtggga atattcacaa ttatttagca tggtatcagc agaaacaggg    600
aaaatctcct cagctcctgg tctataatgc aaaaaccttg cagatggtg tgccatcaag     660 gttcagtggc agtggatcag gaacacaata ttctctcaag atcaacagcc tgcagcctga    720
agattttggg agttattact gtcaacattt tggagtact ccgtacacgt tcggagggg     780 gaccaagctg gaaataaaac gggctgatgc tgcggccgct tctagagggc ccttcgaagg    840
taagcctatc cctaaccctc tcctcggtct cgattctacg cgtaccggtc atcatcacca    900
tcaccacgga ggtgcatgct ga                                            922

<210> SEQ ID NO 19
<211> LENGTH: 939
<212> TYPE: DNA
<213> ORGANISM: Artificial Sequence
<220> FEATURE:
<223> OTHER INFORMATION: C terminal Q-tag (pHOG-LIBS-His-gga-QQ)

<400> SEQUENCE: 19
atgaagttat gcatattact ggccgtcgtg gcctttgttg gcctctcgct cgggagatcg     60
gccatggcgc aggtgcagct gcagcagtct gggggaggct tagtgaagcc tggagggtcc    120
ctgaaactct cctgcgcagc ctctggattc actttcagta gctatatcat gtcttgggtt    180
cgccagactc cggagaagag gctggagtgg gtcgcaacca ttagaagtgg tggtgataac    240
acctactatc cagacagtgt gaaggtgcga ttcaccatct ccagagacaa tgccaagaac    300
aagttgtacc tgcaaatgag cagtctgagg tctgaggaca cggccttgta ttactgtgca    360
atctactatg gtaactacgg ggggcttgct tactggggcc aagggactct ggtcactgtc    420
tctgcagcca aaacgacacc caagcttgaa gaaggtgaat tttcagaagc acgcgtagat    480
atcttgatga cccaatctcc agcctcccta tctgcatctg tgggagaaac tgtcaccatc    540
acatgtcgag caagtgggaa tattcacaat tatttagcat ggtatcagca gaaacaggga    600 aaatcctcc agctcctggt ctataatgca aaaaccttag cagatggtgt gccatcaagg    660
ttcagtggca gtggatcagg aacacaatat tctctcaaga tcaacagcct gcagcctgaa    720
gattttggga gttattactg tcaacatttt tggagtactc cgtacacgtt cggagggggg    780
accaagctgg aaataaaacg ggctgatgct gcggccgctt ctagagggcc cttcgaaggt    840
aagcctatcc ctaaccctct cctcggtctc gattctacgc gtaccggtca tcatcaccat    900
caccacggag gtgcaccgaa acctcaacag ttcatgtga                          939
```